US012708659B2

(12) United States Patent
Reddy

(10) Patent No.: US 12,708,659 B2
(45) Date of Patent: Aug. 18, 2026

(54) POLYPHENOLIC INSULIN

(71) Applicant: Robert R. Reddy, Frederick, MD (US)

(72) Inventor: Robert R. Reddy, Frederick, MD (US)

(73) Assignee: KIMBALL WESTWARD LLC, Sheridan, WY (US)

( * ) Notice: Subject to any disclaimer, the term of this patent is extended or adjusted under 35 U.S.C. 154(b) by 746 days.

(21) Appl. No.: 18/019,576

(22) PCT Filed: Aug. 4, 2021

(86) PCT No.: PCT/US2021/044534

§ 371 (c)(1),
(2) Date: Feb. 3, 2023

(87) PCT Pub. No.: WO2022/031842

PCT Pub. Date: Feb. 10, 2022

(65) Prior Publication Data

US 2023/0321197 A1 Oct. 12, 2023

Related U.S. Application Data

(60) Provisional application No. 63/113,789, filed on Nov. 13, 2020, provisional application No. 63/060,668, filed on Aug. 4, 2020.

(51) Int. Cl.
*A61K 38/28* (2006.01)
*A61K 47/10* (2017.01)

(52) U.S. Cl.
CPC .............. *A61K 38/28* (2013.01); *A61K 47/10* (2013.01)

(58) Field of Classification Search
CPC ......... A61K 38/28; A61K 47/10; C07K 14/62
See application file for complete search history.

(56) References Cited

U.S. PATENT DOCUMENTS 7,026,284 B2 4/2006 Gen
2012/0225811 A1* 9/2012 Robinson ............. C07K 1/1136 530/399
2013/0338064 A1 12/2013 Liu et al.

FOREIGN PATENT DOCUMENTS

KR 100434394 B1 6/2004

OTHER PUBLICATIONS

Chen et al., "Biological Relevance of the Interaction Between Resveratrol and Insulin", Food Biophysics (2013), 8 Pages.
Ostergaard et al., "The ABC of Insulin: The Organic Chemistry of a Small Protein", Chemistry—A European Journal (2020), 17 Pages.
Sirangelo et al., "Hydroxytyrosol Inhibits Protein Oligomerization and Amyloid Aggregation in Human Insulin", International Journal of Molecular Sciences (2020), 16 Pages.
Haghighi-Poodeh et al., "Monocyclic phenolic compounds stabilize human insulin and suppress its amorphous aggregation: In vitro and in vivo study," Biochemical and Biophysical Research Communications 518 (2019) 362-367.
Mukherjee et al., "Prion-derived tetrapeptide stabilizes thermolabile insulin via conformational trapping," iScience 24, 102573, Jun. 25, 2021, 13 pages.
Pathak et al., "Resveratrol as a nontoxic excipient stabilizes insulin in a bioactive hexameric form," Journal of Computer-Aided Molecular Design (2020) 34:915-927.
Smith et al., "A novel complex of a phenolic derivative with insulin: Structural features related to the T → R transition," Protein Science (1996), 5:1502-1511.
Weiss et al., "Insulin Biosynthesis, Secretion, Structure, and Structure-Activity Relationships," NCBI Bookshelf; accessed Oct. 14, 2020; 45 pages.

* cited by examiner

*Primary Examiner* — Gyan Chandra
(74) *Attorney, Agent, or Firm* — Martin Fessenmaier; Umberg Zipser LLP

(57) ABSTRACT

Insulin complexes are stabilized using a ligand that increases binding interactions between the insulin monomers, and particularly between the B-chains of two adjacent insulin monomers. Particularly preferred ligands are polyphenols, and insulin complexes are typically in the R-state and may therefore also include metal cations and a small phenolic compound in a binding site that is distinct from the polyphenol binding site.

20 Claims, 8 Drawing Sheets

A

B

Condition A: Sample: 50 mM Tris pH 7.5, 0.3 mM $CoCl_2$, 50 mM phenol, 0.6 mM Insulin (96 hours); Running Buffer: 10 mM Tris pH 7.5, 140 mM NaCl

Conditions B and C: Sample: 50 mM Tris pH 7.5, 0.3 mM $CoCl_2$, 50 mM phenol, 0.6 mM Insulin, and 0.4 mM quercetin (96 hours); Running Buffer: 10 mM Tris pH 7.5, 140 mM NaCl Element 1

Element 2

Element 3

Element 4

Element 5

POLYPHENOLIC INSULIN

CROSS-REFERENCE TO RELATED APPLICATIONS

This application is an International Application which claims priority to U.S. Provisional Patent Application No. 63/113,789, filed Nov. 13, 2020 and U.S. Provisional Patent Application No. 63/060,668, filed Aug. 4, 2020, which are all hereby incorporated in their entirety by reference.

FIELD OF THE INVENTION

The field of the invention is pharmaceutical compositions and methods for stabilizing insulin, especially as it relates to insulin complexes comprising one or more polyphenols.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Insulin is the primary anabolic hormone in mammalian physiology. The primary structure of insulin consists of two separate peptide chains, the A-chain and B-chain, which are covalently linked by disulfide bonds. Native insulin is stored and secreted from β-islet cells within the pancreas. Inside granular structures found within β-islet cells, insulin naturally oligomerizes with two zinc ions forming a six insulin sub-unit, two zinc ion, hexameric complex. Recombinant insulin has been known for several decades. However, despite its relatively simple chemical structure and small molecular weight, preparation of a therapeutic insulin with desirable physiological and pharmacokinetic and pharmacodynamic properties remains a challenge. Several insulin analogs have been developed to improve glycemic control in diabetic patients, and specific changes in the insulin structure through chemical or molecular biological modifications were shown to lead to variations in its pharmacokinetics and bioavailability.

For example, insulin is now commercially available as rapid-acting, short-acting, intermediate-acting, and long-acting Neutral Protamine Hagedorn (NPH) formulations, which can each be combined with unmodified human insulin to obtain a specific physiological activity profile. Among other options, rapid-acting insulin modifications allow larger quantities of monomeric insulin to be available with a typical onset of action from 5 to 15 min after s.c. injection and biological effect lasting up to 4-6 hours. In such insulin forms, one or two amino acids are typically changed from the wildtype sequence to weaken the self-association into higher order complexes to so facilitate absorption and signaling at the receptor level (e.g., insulin aspart (Novo Nordisk), insulin lispro (Eli Lilly) and insulin glulisine (Sanofi-Aventis)). Other short-acting formulations include unmodified human insulin such as Humulin (Eli Lilly) or Novolin (Novo Nordisk), which typically start working within 30 min and remain active for about 5 to 8 h.

In this context it must be appreciated that insulin in almost all pharmaceutical formulations is in form of a hexameric complex, which is not physiologically active. To exert biological activity, the hexameric complex must first dissociate into dimers and subsequently to monomers. Making use of this change in association has enabled the formulation of insulin that could provide a continuous or steady-state level of insulin that helps avoid multiple injections, and a variety of attempts were made along these lines. For example, intermediate-acting NPH insulin was formulated with an onset ranging from 1 to 2 h and a duration from 18 to 24 h by addition of a protamine, resulting in a slower release from the injection site and with that an extended time of action.

In another approach to extend the action of insulin, the protein can be modified to shift the isoelectric point towards a more neutral pH. Such shift is typically achieved by addition of positively charged amino acids to the B-chain of insulin. As a result, the so modified insulin remains less soluble at the neutral pH of the injection site, forms microprecipitates at a physiological, neutral pH and is then gradually released into circulation, thereby giving rise to a long-term therapeutic level of insulin. One such long-acting analog is insulin glargine (Lantus, Sanofi-Aventis), where glycine is substituted for asparagine at position A21 in human insulin and where two arginine residues to the C-terminus of the B-chain were added. Another long-acting analog is insulin detemir (Levemir, Novo Nordisk) that has a $C_{14}$ fatty acid side chain added to the B-chain at position B29. This modification enables detemir to reversibly bind with albumin and to form multimeric complexes within subcutaneous tissue, which prolongs its duration of action.

Similarly, another approach to extend the action of proteins relies on a modification of proteins to decrease their solubility in a physiological salt solution by reacting the proteins with epigallocatechin gallate to form a cross-linked protein complex (see U.S. Pat. No. 7,026,284). Examples of such proteins used to form the cross-linked protein complex include among others insulin. However, while complexes described in the US '284 patent render the cross-linked protein complexes more immune tolerable, the cross-linked protein complexes may not be suitable for therapeutic administration such as with insulin due to the tight disordered complexation of the protein components and their very slow release of the insulin monomers for their therapeutic effect.

In still other approaches for long-acting analog, an ultralong-acting insulin analog (insulin degludec (Tresiba, Novo Nordisk)) is made by deletion of the B30 threonine and the addition of a $C_{16}$ fatty diacid to B29 lysine with an additional glutamic acid as a spacer. This structure promotes formation of multi-hexamers in subcutaneous tissue, resulting in a long and flat extended insulin action profile. In addition, combinations of various forms of short and long acting insulin analogs are known to further tailor activity profiles. Examples of such mixtures include insulin aspart, degludec/insulin aspart, detemir/insulin aspart, etc., which advantageously cover postprandial need for insulin.

In addition to changing or adding amino acids or acylation, long-lasting pharmaceutical insulin formulations have previously been shown to be improved, in terms of biological effect and increased half-life, by addition of metal ions and small phenolic compounds such as meta-cresol, phenol, resorcinol, methylparaben, and others. The increased pharmaceutical half-life of these metal ion and small phenolic potentiated insulin formulations has been directly attributed to the ability of small phenolic compounds to bind within a small phenolic compound binding pocket found between insulin monomers within larger hexameric, and other oligomeric, insulin complexes. This binding of small phenolic compounds within the small phenolic compound binding pocket located in regions of hexameric insulin dimer-dimer interface is attributed to hydrogen bonding of small phenolic compounds to specific amino acids of the A-chain in the monomers ($A_6$ carbonyl oxygen and $A_{11}$ amide hydrogen). Moreover, this binding also induces a structural change in the monomeric insulin.

Consequently, a conformational change occurs in the hexameric and other oligomeric insulin complexes. Once a small phenolic compound is bound within the small phenol binding pockets within the hexameric insulin complex, there is an increase in the alpha helical character of the amino-terminus of the B-chain of monomeric insulins within oligomeric insulin. Once the amino-terminus of the B-chain of insulin monomers within hexametric insulin complex becomes more alpha helical in nature, the organization of insulin monomers around a metal center, having three-fold rotational symmetry, within hexameric insulin complexes changes. In addition to the reduction in solvent access, the conformational change in insulin monomers surrounding a metal center also allows for the metal ion to change from an octahedral coordination state to a tetrahedral coordination state. This change in metal coordination state can happen up to two times in hexameric insulin complexes since the complex has two metal atoms located within two centers of 3-fold rotational symmetry. Each of the three insulin monomers around one of two metal ions within hexameric insulin complexes binds the metal ion by their histidines found at position 10 of the insulin monomer B-chain in the consensus amino acid sequence of human insulin.

Literature designates the name $T_6$ hexameric insulin to the hexameric insulin complex in which both metal ions within the hexameric insulin complex have an octahedral coordination state. An exemplary illustration of one metal ion center in an octahedral coordination state, shown from the top to demonstrate a center of 3-fold rotational symmetry, in hexameric insulin can be seen in FIG. 1, Element 1, panel A. On the other hand, FIG. 1, Element 1, panel C, illustrates a zinc ion in an octahedral coordination state bound to hexameric insulin. The overall coordination of a divalent metal ion within a metal ion center of a hexameric insulin 3-fold rotational symmetry, such as zinc, changes from octahedral to tetrahedral, three coordinated beta-chain histidines, and one coordination with a negative ion, shown as "L" in FIG. 1, Element 2, panel D, when the insulin monomers within a hexameric insulin complex have a small phenolic compound bind within the small phenolic binding pockets of hexameric insulin. In FIG. 1 the line drawing made to resemble the top views of hexameric insulin compares the two different species: $T_3$ in FIG. 1, element 1, panel A; $R_3$ in FIG. 1, element 2, panel B. FIG. 1, element 3, panel B points to the three locations, within one $R_3$ hexameric insulin center of 3-fold rotational symmetry, where phenol, or other small phenolic compounds, bind and induce a conformational change within the amino-terminal B-chains of insulin monomers within R-state hexameric insulin. Literature designates the name $T_3R_3$ hexameric insulin to the hexameric insulin complex in which one of two metal ions within one of two centers of 3-fold rotational symmetry within hexameric insulin is tetrahedrally coordinated, and the other metal ion within the other center of 3-fold rotational symmetry has not seen the insulin conformational changes induced by a small phenolic compound binding, and the metal ion in that location is therefore octahedrally coordinated.

When both metal ions within both centers of 3-fold rotational symmetry within the hexameric insulin complex are tetrahedrally coordinated, literature has designated the name for this hexameric insulin complex hexameric $R_6$ insulin. The relative resistance of hexameric insulin species to dissolve into dimers and monomers with time, in physiologically relevant conditions of ionic strength and pH, from lower hexameric stability (T-state) to higher hexameric stability (R-state) is: $T_6 < T_3R_3 < R_6$.

Consequently, the biological effect of insulin complexes is in most cases a function of the stability of the insulin complex, and various modifications have been made to insulin to affect the stability. However, despite the relatively large number of different insulin preparations, various disadvantages nevertheless remain. Most significantly, where the native insulin is chemically or recombinantly modified, such modified forms fail to parallel the biological action of unmodified forms. Moreover, in at least some instances, the modified forms of insulin can become immunogenic over time and as such present an additional risk to the patient.

Thus, even though various compositions and methods of modifying insulin are known in the art, all or almost all of them suffer from several drawbacks. Therefore, there remains a need for compositions and methods for improved compositions and methods that extend insulin action.

SUMMARY OF THE INVENTION

The inventive subject matter is directed to various compositions and methods of insulin in which the stability of an insulin complex is increased by binding of a ligand, and most preferably a polyphenol, to a binding site that is proximal to an interface formed by respective B-chains of monomeric insulin, and where binding of the ligand increases the binding interaction between the first and second insulin monomers. Most typically, the stabilized insulin complexes will include, in addition to the polyphenol, a ligand (e.g., phenolic compound such as phenol) bound to a small phenol binding pocket that is distinct from the polyphenol binding site. Viewed from a different perspective, contemplated stabilized insulin complexes will include both, a small phenolic ligand and a polyphenolic ligand, both non-covalently bound to distinct sites in the complexes as described in more detail herein. Advantageously, increased binding interaction affords various benefits, including increased overall stability of the complex, extended biological effect, increased signaling, and reduction of amyloid formation at the injection site, Therefore, in one aspect of the inventive subject matter, the inventors contemplate a pharmaceutical composition that comprises an insulin complex having a plurality of insulin monomers, in which each insulin monomer includes an A-chain and a B-chain coupled together via disulfide bonds. A polyphenol (e.g., a flavonol, a flavanol, or other flavonoids, a stilbenoid polyphenol, or a curcuminoid polyphenol) is non-covalently bound to an apical area of an interface that is formed by respective B-chains of first and second insulin monomers in the complex.

Most typically, the insulin complex will comprise six or twelve insulin monomers, and has a $T_3R_3$ or $R_6$ conformation. Thus, the insulin complex may further comprise a divalent metal cation and/or a small phenolic ligand in which two hydrogen bonds from the A-chain of the insulin monomers engage the phenolic hydroxyl group from the $A^6$ carbonyl oxygen and $A^{11}$ amide hydrogen.

While not limiting to the inventive subject matter, the insulin monomer is preferably a human insulin monomer. As will be readily appreciated, the insulin monomer(s) may also be modified to allow for increased biological activity. For example, at least one of the insulin monomers in the complex may have one or more amino acid substitutions (relative to a corresponding wild-type) that increases serum half-life of the insulin complex. Alternatively or additionally, at least one of the insulin monomers in the complex may have a chemical modification that increases serum half-life of the insulin complex.

It is further contemplated that the polyphenol binds to at least one (and more typically two) amino acid side chains of an amino acid in a B-chain of the first insulin monomer and to at least one amino acid side chain of another amino acid in a B-chain of the second insulin monomer to thereby increase a binding interaction between the first and second insulin monomers. Among other options, the polyphenol may bind to $B^{5His}$ and $B^{26Tyr}$ of the first insulin monomer and $B^{16Tyr}$ of the second insulin monomer, and at least part of the apical area of the interface is solvent exposed.

Therefore, and viewed from a different perspective, the inventor contemplates a method of producing a pharmaceutical composition that comprises insulin. Such method may include a step of providing an insulin complex that has a plurality of insulin monomers with each insulin monomer having an A-chain and a B-chain coupled together via disulfide bonds. In another step, the insulin complex is combined with a polyphenol (e.g., a flavonol, a flavanol, or other flavonoid, a stilbenoid polyphenol, or a curcuminoid polyphenol) to produce a stabilized insulin complex, wherein the polyphenol in the stabilized insulin complex is non-covalently bound to an apical area of an interface formed by respective B-chains of a first and a second insulin monomer in the insulin complex.

With respect to the insulin complex, the polyphenol, additional components such as metal ions and/or small phenolic ligands, etc., the same considerations as noted above apply.

In another aspect of the inventive subject matter, the inventor also contemplates a method of extending a biological effect of an insulin complex. Such methods will typically include a step of stabilizing the insulin complex with a ligand that binds to at least one amino acid side chain of an amino acid in a B-chain of a first insulin monomer and to at least one amino acid side chain of another amino acid in a B-chain of a second insulin monomer to thereby increase a binding interaction between the first and second insulin monomers. Most typically, the increased binding interaction extends the in vivo biological effect of the insulin complex as compared to a non-stabilized insulin complex. In at least some examples, the biological effect of the insulin complex is extended by at least 10%.

As will be readily recognized, preferred ligands are polyphenol ligands such as a flavonol, a flavanol, or other flavonoids, a stilbenoid polyphenol, or a curcuminoid polyphenol. Most typically, the step of stabilizing is performed in vitro, and the stabilized insulin complex is administered by injection. However, it is also contemplated that the step of stabilizing may be performed in vivo by co-administration of the insulin complex and the compound (and/or optionally the small phenolic compound such as sodium benzoate or 4-hydroxybenzoic acid), wherein the insulin complex is administered by injection and wherein the compound(s) is/are administered orally.

Additionally, it is contemplated that the insulin complex comprises at least one human insulin monomer. Where desired, the insulin complex may comprise one or more insulin monomers that has a chemical modification that increases serum half-life of the insulin complex and/or one or more amino acid substitutions relative to a corresponding wild-type that increases serum half-life of the insulin complex. Additionally it is contemplated that a plurality of preformed insulin complexes may be subcutaneously injected or otherwise administered together so as that the separate microcrystalline or micro aggregate insulin complexes release monomeric insulin in accordance with their respective individual complex dissociation kinetics under local in vivo conditions.

Therefore, the inventor also contemplates a method of improving insulin serum profiles and/or increasing stability of a long acting insulin complex that includes a step of providing a long acting insulin complex comprising a plurality of insulin monomers and complexes as described herein, each insulin monomer comprising an A-chain and a B-chain coupled together via disulfide bonds. It is generally contemplated that at least one insulin monomer in such method has (a) a chemical modification that increases serum half-life of the insulin complex and/or (b) one or more amino acid substitutions relative to a corresponding wild-type that increases serum half-life of the insulin complex. In another step, the insulin complex is combined with a ligand to produce a stabilized insulin complex, wherein the ligand in the stabilized insulin complex is non-covalently bound to an apical area of an interface formed by respective B-chains of a first and a second insulin monomer in the insulin complex.

Most preferably, the ligand is a polyphenol such as a flavonol, a flavanol, or other flavonoid, a stilbenoid polyphenol, or a curcuminoid polyphenol. It is also generally contemplated that the long acting insulin complex comprises six or twelve insulin monomers, and that the long acting insulin complex has a $T_3R_3$ or $R_6$ conformation. In at least some embodiments, the long acting insulin complex further comprises a divalent metal cation and/or a phenolic ligand in which two hydrogen bonds engage the phenolic hydroxyl group from the $A^6$ carbonyl oxygen and $A^{11}$ amide hydrogen. Exemplary long acting insulin forms include NPH insulin, Lente (L) insulin, Ultralente (U) insulin, Lantus insulin, Glargine insulin, Levemir insulin, and Detemir insulin. It is further contemplated that the step of stabilizing may be performed in vitro prior to administration of the insulin complex. Importantly, the $T_3R_3$ or $R_6$ conformation of the insulin complex due to interaction with the polyphenol, yet without cross-linking, leads to improved stabilization of the insulin complex while still allowing the monomers of the insulin complex to disassociate for their therapeutic effect.

In yet another aspect of the inventive subject matter the inventor contemplates a method of increasing insulin signaling at an insulin receptor. Such methods will preferably include a step of contacting the insulin receptor with an insulin monomer-polyphenol complex, wherein the insulin monomer in the insulin monomer-polyphenol complex comprises an A-chain and a B-chain coupled together via disulfide bonds, wherein the polyphenol is non-covalently bound to the insulin monomer.

Most typically, the insulin monomer-polyphenol complex is derived (in vivo) from a hexameric or dodecameric insulin complex, preferably formed from human insulin monomers. As noted above, especially contemplated polyphenols include a flavonol, a flavanol, or other flavonoid, a stilbenoid polyphenol, and a curcuminoid polyphenol. In typical aspects, the insulin monomer-polyphenol complex increases signaling strength as compared to an insulin monomer without the polyphenol and/or increases signaling duration as compared to an insulin monomer without the polyphenol.

In still another aspect of the inventive subject matter the inventor contemplates method of increasing storage stability of an insulin complex that includes a step of providing an insulin complex comprising a plurality of insulin monomers, each insulin monomer comprising an A-chain and a B-chain coupled together via disulfide bonds. In a further step, the insulin complex is combined with a polyphenol to produce a stabilized insulin complex, wherein the polyphenol in the stabilized insulin complex is non-covalently bound to an apical area of an interface formed by respective B-chains of a first and a second insulin monomer in the insulin complex. Most typically, the stabilized insulin complex has at least 10% increased storage stability as compared to a corresponding insulin complex without the polyphenol. With respect to the insulin complex and monomers, the polyphenol, optional metal ions and/or small phenolic ligands, the same considerations as noted above apply.

Notably, in an additional aspect of the inventive subject matter, the inventor also contemplates a method of reducing insulin amyloid formation. Such method includes a step of stabilizing an insulin complex with a ligand that binds to at least one amino acid side chain of an amino acid in a B-chain of a first insulin monomer and to at least one amino acid side chain of another amino acid in a B-chain of a second insulin monomer to thereby increase a binding interaction between the first and second insulin monomers, wherein the increased binding interaction reduces insulin amyloid formation in vivo upon injection as compared to a non-stabilized insulin complex.

Most preferably, the ligand is a polyphenol such as a flavonol, a flavanol, or other flavonoid, a stilbenoid polyphenol, or a curcuminoid polyphenol. It is further contemplated that the step of stabilizing is performed in vitro, and that the stabilized insulin complex is administered by injection. Most typically, the insulin complex comprises at least one human insulin monomer. Where needed or desired, the insulin complex may comprise at least one insulin monomer that has a chemical modification that increases serum half-life of the insulin complex and/or one or more amino acid substitutions relative to a corresponding wild-type that increases serum half-life of the insulin complex.

In view of the above, a method of reducing blood glucose in a subject in need thereof is therefore contemplated that includes a step of administering a pharmaceutical composition as presented herein to the subject to thereby reduce the blood glucose. As will be appreciated, such methods may also include a step of co-administering a polyphenol-containing composition to the subject. Viewed from a different perspective, the inventor also contemplates a polyphenol for use in the treatment of diabetes with insulin, wherein the insulin is administered as an insulin complex or mixture of different insulin complexes, comprising a plurality of insulin monomers, each insulin monomer comprising an A-chain and a B-chain coupled together via disulfide bonds, and wherein the polyphenol is non-covalently bound to an apical area of an interface formed by respective B-chains of a first and a second insulin monomer in the complex.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
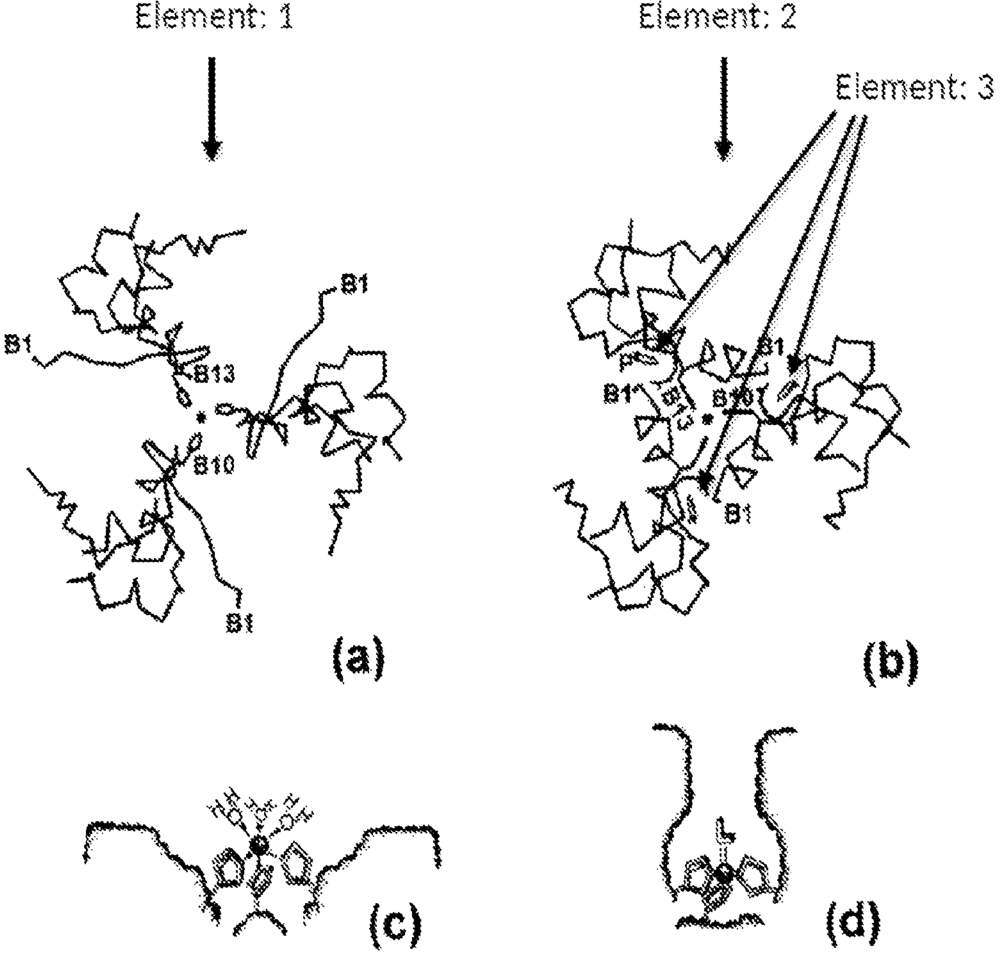
FIG. 1 is a schematic illustration of an insulin complex with an octahedral coordination state (panels (a) and (c)) and a tetrahedral coordination state (panels (b) and (d)).

The inventor has now discovered various compositions, methods, and uses related to structurally stable and long-lasting soluble oligomeric insulin that has various advantages heretofore not realized with known insulin compositions.

As is well recognized, maintenance of insulin levels by delivery of crystalline or partially crystalline pharmaceutical insulin formulations (typically hexameric insulin or dodecameric insulin) is critical for diseases related to glycemic control, such as type one and type two diabetes. In most cases, biologically active monomeric insulin is released from hexameric or higher complexes that are inactive to so extend biological activity. To that end, insulin has been modified by substitution of selected amino acids and/or acylation of reactive groups in insulin, and examples of such modified forms include NPH insulin, Lente (L) insulin, Ultralente (U) insulin, Lantus insulin, Glargine insulin, Levemir insulin, and Detemir insulin. While such forms have shown desirable extension of biological activity, various disadvantages nevertheless remain, including potential immunogenicity, denaturation, covalent dimerization, and/or deamidation of insulin during storage before use.

Advantageously, these and other disadvantages can now be reduced or even entirely avoided by preparing insulin complexes to which is bound a polyphenolic ligand that not only stabilizes the insulin complexes and increases signaling at the insulin signal transduction level, but that also reduces amyloid formation at the site of injection. In most preferred embodiments, and as discussed in more detail below, the insulin complexes contemplated herein will include a polyphenol ligand that is non-covalently bound to polyphenol binding pocket located in an apical area of an interface formed by respective B-chains of a first and a second insulin monomer in the complex. Typically, but not necessarily, the insulin complex is crystalline and will release insulin monomers or dimers into the circulation. As the polyphenol ligand increases the binding interaction between insulin monomers, a more delayed release of mono and dimeric insulin is realized along with a higher storage stability and stability at the site of injection. In still further beneficial aspects of the inventive subject matter, the released insulin monomer or dimer will have the polyphenol still bound, which enhances biological activity as compared to insulin without the polyphenolic ligand.

In one embodiment on the inventive subject matter, a hexameric insulin complex containing six unmodified human insulin monomers containing phenol in the small phenolic binding pocket is further stabilized by quercetin where the quercetin is non-covalently bound to an apical area of an interface formed by respective B-chains of a first and a second insulin monomer in the insulin complex.

However, it should be appreciated that the insulin need not be limited to unmodified human insulin, but that various other sources are also deemed suitable for use herein, including porcine, bovine, equine, murine, etc. Moreover, it should be appreciated that one or more of the insulin monomers may also be modified (e.g., by amino acid substitution or addition, and/or by chemical modification. Additionally, multiple forms of single type insulin complexes are envisioned, being native human insulin or modified, formed individually with one or more polyphenol types mixed with a plurality of similarly formed insulins. As such, it should be recognized that all forms of insulin, including currently commercially available forms of insulin are deemed suitable for use herein, including NPH insulin, Lente (L) insulin, Ultralente (U) insulin, Lantus insulin, Glargine insulin, Levemir insulin, and Detemir. Likewise, it should be appreciated that polyphenolic insulin (i.e., insulin with a polyphenol non-covalently bund thereto) may be combined with any other form of insulin to tailor to a specific activity profile.

Thus, pharmaceutical compositions containing polyphenolic insulin are especially contemplated herein. Most typically, the polyphenolic insulin or composition containing polyphenolic insulin will be formulated as crystalline, amorphous, dissolved, or lyophilized forms, most typically for injection.

With respect to suitable polyphenols, it should be appreciated that all polyphenols are deemed suitable for use herein. Therefore, suitable polyphenols include various flavonols (e.g., quercetin, rhamnazin, rhamnetin, galangine, etc.), various flavanols (e.g., catechin, epicatechin, epigallocatechin, mesquitol, etc.), various stilbenoid polyphenols (e.g., resveratrol, pterostilbene, pinosylvine, etc.), and various curcuminoid polyphenols (e.g., curcumin, desmethoxycurcumin, etc.). Moreover, while naturally occurring compounds are generally preferred, it should be appreciated that numerous synthetic ligands are also contemplated herein so long as such ligands also occupy the polyphenolic binding pocket as described in more detail below.

Figure 7:
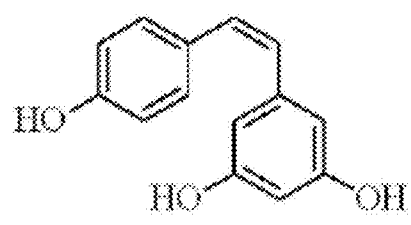
FIG. 7 depicts various polyphenol ligands contemplated for use herein. The polyphenol ligands depicted are as follows: Element 1—quercetin, IUPAC name: 2-(3,4-dihydroxyphenyl)-3,5,7-trihydroxy-4H-chromen-4-one); Element 2—catechin, IUPAC name: (2R, 3S)-2-(3,4-Dihydroxyphenyl)-3,4-dihydro-2H-chromene-3,5,7-triol); Element 3—cis-resveratrol, IUPAC name: 3,5,4'-trihydroxy-cis-stilbene; Element 4—trans-resveratrol, IUPAC name: 3,5,4'-trihydroxy-trans-stilbene; Element 5—curcumin, IUPAC name: 1E,6E)-1,7-Bis(4-hydroxy-3-methoxyphenyl(hepta-1,6-diene-3,5-dione.
Figure 7:
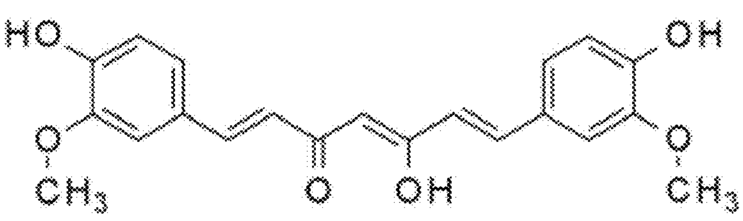

Therefore, and among other suitable options, preferred polyphenols for preserving, stabilizing, and/or potentiating therapeutic oligomeric $R_6$ insulin oligomers include flavonoids such as the flavonol quercetin (FIG. 7, element 1, IUPAC name: 2-(3,4-dihydroxyphenyl)-3,5,7-trihydroxy-4H-chromen-4-one) and other flavonoids, or compounds of the flavonol class of flavonoids, or synthetically engineered chemical versions of the flavonol class of flavonoids. Other preferred chemical agents include the flavonoid catechin (FIG. 7, element 2, IUPAC name: (2R, 3S)-2-(3,4-Dihydroxyphenyl)-3,4-dihydro-2H-chromene-3,5,7-triol) and various other flavanol class flavonoids, or synthetically engineered chemical versions of the flavanol class of flavonoids. Still other preferred chemical agents include cis-resveratrol (FIG. 7, element 3, IUPAC name: 3,5,4'-trihydroxy-cis-stilbene) and trans-resveratrol (FIG. 7, element 4, IUPAC name: 3,5,4'-trihydroxy-trans-stilbene) and other stilbenoid polyphenols, or synthetically engineered chemical versions of stilbenoid polyphenols. Further preferred chemical agents include curcumin (FIG. 7, element is 5, IUPAC name: 1E,6E)-1,7-Bis(4-hydroxy-3-methoxyphenyl (hepta-1,6-diene-3,5-dione) and other examples of the curcuminoid class of polyphenols, or synthetically engineered chemical versions of the curcuminoid class of polyphenols.

To this end, suitable polyphenolic compound, include, but are not limited to, theaflavin, EGCG, ellagic acid, catechin, 3,3'-diindolylmethane, quercetin, caffeic acid, cyanidin, curcumin, resveratrol, delphinidin, pelargonidin, peonidin, malvidin, petunidin, chrysanthemin, cyanidin-3,5-O-diglucoside, malvidin glucoside-ethyl-catechin, malvidin-3-O-(6-p-coumaroyl) glucoside, myrtillin, oenin, oxovitisin a, pelargonin, peonidin-3-O-glucoside, vitisin A (pyranoanthocyanin), vitisin B (pyranoanthocyanin), pinotin A, ethyl caffeate, fertaric acid, ferulic acid, coumarin, phyllodulcinol, coumestrol, wedelolactone, plicadin, enterodiol, enterolactone, lariciresinol, matairesinol, guibourtinidol, mesquitol, robinetinidol, fisetinidol, gallocatechol, eriodictyol, hesperetin, liquiritigenin, naringenin, pinocembrin, sterubin, hesperidin, engeletin, luteolin, tangeretin, chrysin, techtochrysin, apigenin, acacetin, genkwanin, baicalein, norwogonin, wogonin, chrysoeriol, diosmetin, norartocarpetin, scutellarein, hispidulin, pectolinarigenin, isoscutellarein, zapotin, tricetin, nepetin, eupatilin, cirsilineol, hypolaetin, sinensetin, nobiletin, primuletin, primetin, echioidinin, negletein, geraldone, tithonine, 6-hydroxyluteolin, pilloin, velutin, artocarpetin, sorbifolin, cirsimaritin, mikanin, zapotinin, cerrosillin, alnetin, corymbosin, pedalitin, nodifloretin, jaceosidin, cirsiliol, eupatorin, onopordin, wightin, nevadensin, xanthomicrol, serpyllin, sudachitin, acerosin, hymenoxin, gardenin D, scaposin, kaempferol, myricetin, isorhamnetin, azaleatin, fisetin, galangin, gossypetin, kaempferide, morin, natsudaidain, pachypodol, rhamnazin, rhamnetin, astragalin, isoquercetin, miquelianin, rutin, azalein, hyperoside, isoquercetin, kaempferitrin, myricitrin, quercitrin, robinin, spiraeoside, xanthorhamnin, amurensin, icariin, troxerutin, coutaric acid, daidzein, genistein, justicidin a, pinoresinol, sesamin, 1,2,3,4,6-pentagalloyl glucose, acutissimin A, castavinol C3, grandinin, grape reaction product, oxycinchophen, rosmarinic acid, secoisolariciresinol, vanillin, xanthohumol, glycitein, secoisolariciresinol diglucoside, procyanidin A2, procyanidin B1, procyanidin B2, procyanidin B3, procyanidin B4, procyanidin C1, astringin, delta-viniferin, epsilon-viniferin, hopeaphenol, pallidol, piceatannol, pterostilbene, piceid, oleanolic acid, ursolic acid, higenamine, or combinations thereof.

Consequently, it should be appreciated that the inventive subject matter is directed to polyphenolic insulin compositions and formulations, and particularly therapeutic oligomeric R-state insulin formulations that contain an additional polyphenolic compound or polyphenolic compounds. In most embodiments, the additional polyphenolic compound or polyphenolic compounds preserve and/or increase the stability of oligomeric R-state insulin prior to therapeutic delivery and even post therapeutic delivery. In further embodiments, the preservation of the insulin oligomeric state is further accomplished by inclusion of metal ions (e.g., $Zn^{2+}$) and/or a small phenolic compound or compounds in addition to the polyphenolic compound or compound. Most typically, the insulin complex is prepared using a buffered solution that may or may not contain a salt in addition to the salt that contains an insulin-coordinating metal ion.

Preferred metal ions suitable for use herein are those that create oligomeric insulin by binding insulin B-chain histidine residues at insulin consensus sequence position 10, when formulated in combination with a small phenolic compound or small phenolic compounds, a polyphenolic compound or compounds, any buffer, any salt, or any other component. Therefore, especially suitable metal ions include divalent metal cation cobalt, as a cobalt chloride salt ($CoCl_2$), and the divalent metal cation zinc as a zinc chloride salt ($ZnCl_2$). Preferred small phenolic compounds suitable for use herein include phenol, meta-cresol, resorcinol, sodium benzoate, 4-hydroxybenzoic acid, and methylparaben. Notably, sodium benzoate and 4-hydroxybenzoic acid were also shown to better preserve insulin hexameric complexes that contained quercetin. Thus, it should be recognized that the stabilized insulin complexes (most typically hexameric complexes) will include a metal cation, a small phenolic ligand, and a polyphenol ligand. In some embodiments, the polyphenol may be quercetin and the phenolic ligand may be sodium benzoate or 4-hydroxybenzoic acid, especially where the insulin complexes contain metal cations. In other embodiments, however, m-cresol is excluded as a small phenolic compound.

Figure 2:
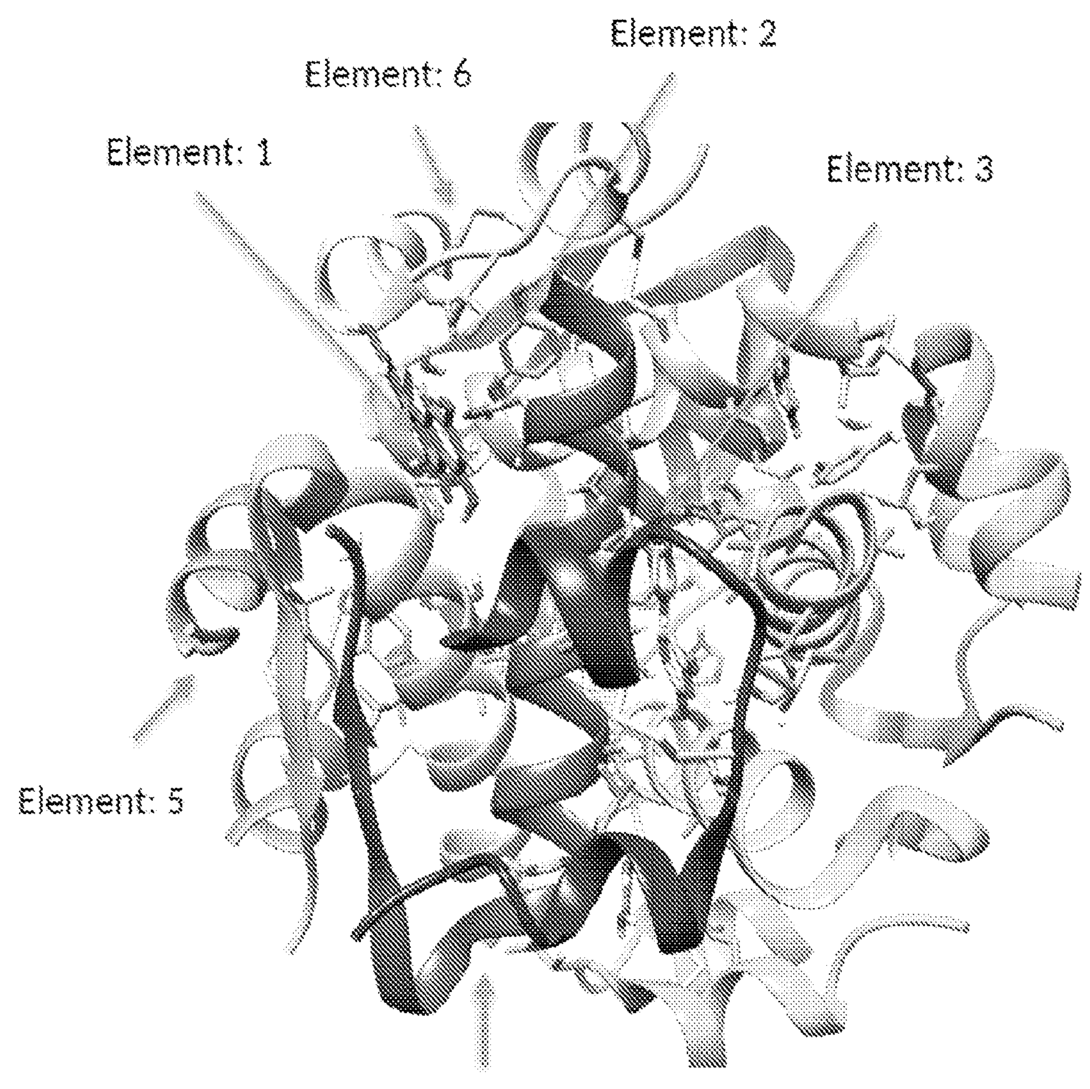
FIG. 2 is an exemplary illustration of an insulin complex with metal ions, small phenolic ligand, and a polyphenolic ligand.

The further addition of a polyphenolic compound or polyphenolic compounds may act to stabilize human insulin variants by binding to a previously undescribed polyphenolic binding pocket found near the monomer-monomer dimer interface of human oligomeric insulin variants (here: an apical area of an interface formed by respective B-chains of a first and a second insulin monomer in the complex as described in more detail below). In this context, it must be appreciated that this polyphenolic binding pocket is distinct from the currently known small phenol binding site. The action of stabilizing the monomer-monomer dimer interface of insulins within oligomeric insulin may act to stabilize hexameric, dodecameric, and other oligomeric forms of R-state insulin to a greater degree than formulations including just buffer, a salt, small phenolic compounds, and metal ions alone. Viewed from a different perspective, the addition of a polyphenolic compound or polyphenolic compounds results in increased stabilization of oligomeric R-state insulin forms, ultimately improving the pharmacokinetics and pharmacodynamics of long-lasting insulin-formulated therapeutics and other insulin-formulated therapeutics and may offer additional utility to biomedical research. Therefore, it should be appreciated that polyphenolic insulin is characterized by the polyphenolic binding pocket as shown in FIG. 2 (element 1 is quercetin located in the polyphenol binding pocket).

The polyphenol binding pockets, when bound to a polyphenol, may act to further stabilize the monomer-monomer dimer interface found between individual insulin monomers within a greater oligomeric insulin structure that may be in form of hexameric or dodecameric R-state insulin oligomers. As previously mentioned, the insulin monomer-monomer dimer interface contains a heretofore undescribed pocket suitable for binding of polyphenolic compounds such as flavinoid compounds and quercetin (FIG. 2, element 1). Molecular docking of quercetin to a hexameric $R_6$ insulin crystallographically determined structure containing resorcinol (FIG. 2, element 2) and zinc (FIG. 2, element 3) has shown that binding of certain polyphenolic compounds including flavonoid compounds and quercetin are energetically favorable. Moreover, energetically favorable binding is seen to occur within the monomer-monomer dimer interface of hexameric $R_6$ insulin (FIG. 2, element 1, between blue insulin monomer [element 4], cyan insulin monomer [element 5], and yellow insulin monomer [element 6]). The specific amino acid residues interacting with polyphenolic compounds, quercetin in the example shown, may be, but are not limited to being, insulin B-chain histidine at position 5 and insulin B-chain tyrosine at position 26 (FIG. 2, blue insulin monomer [element 4]) in one insulin monomer, and insulin B-chain tyrosine at position 16 (FIG. 2, cyan insulin monomer [element 5]) in the second monomer of a monomer-monomer dimer pair within oligomeric insulin.

Figure 6:
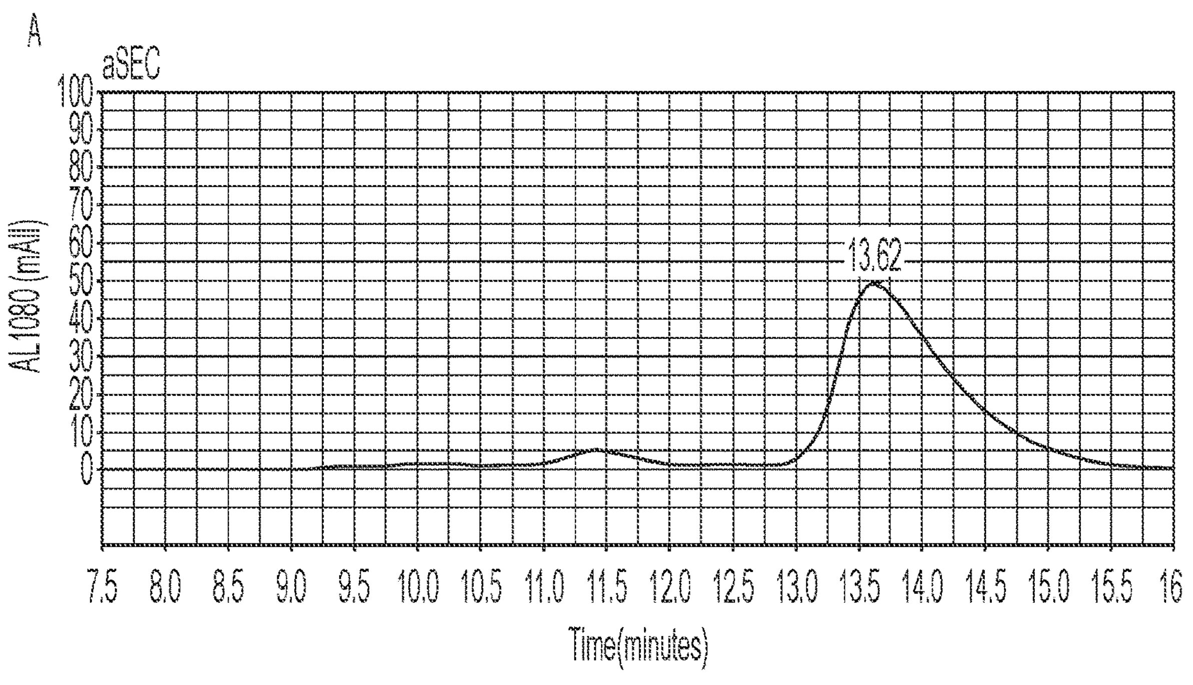
FIG. 6 depicts exemplary 280 nm absorbance elution profiles of insulin plus phenol (a) and insulin plus phenol and quercetin (b), and an exemplary 574 nm absorbance of insulin plus phenol and quercetin (c).
Figure 6:
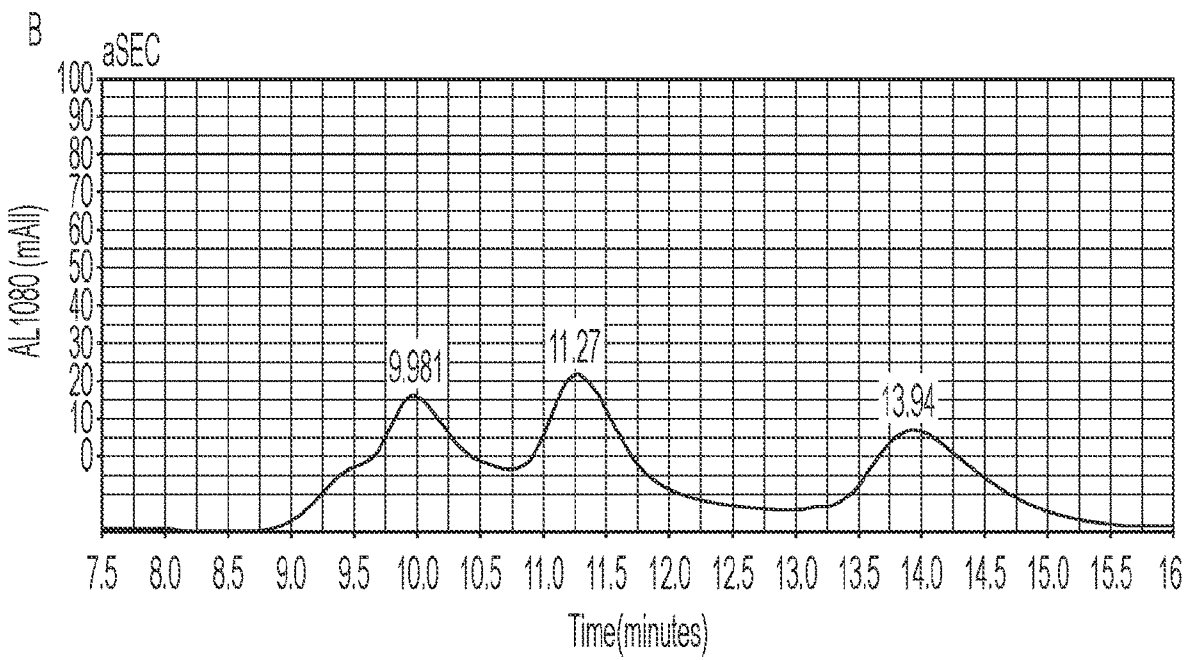
Figure 6:
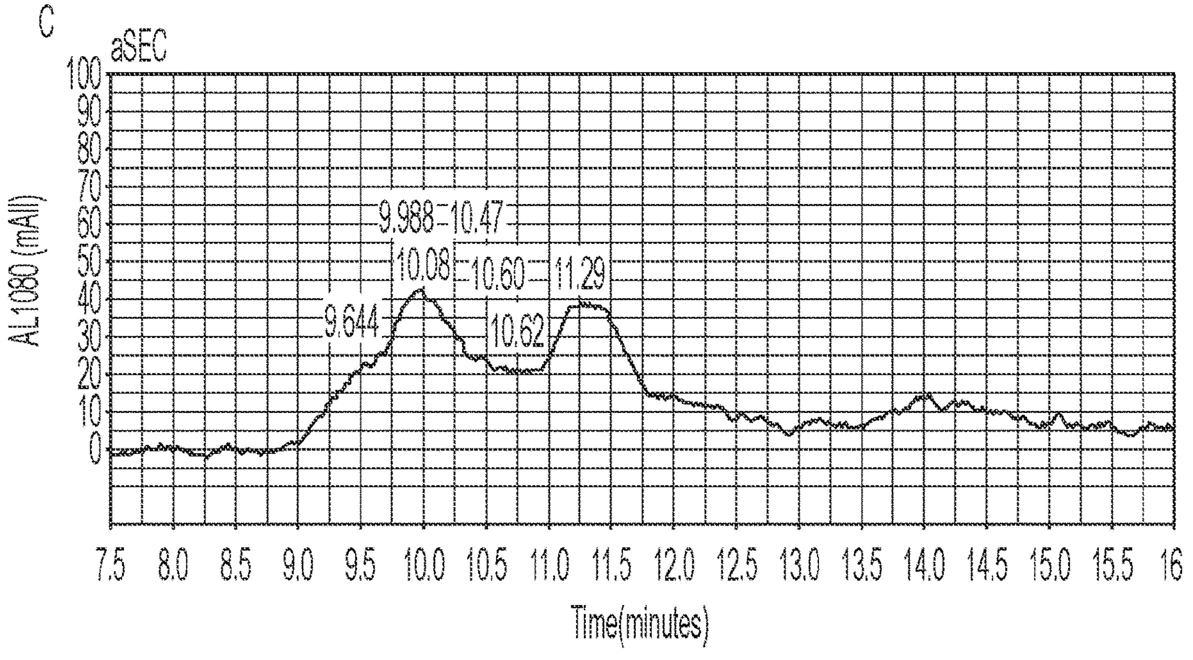

The direct interaction between aromatic residues in adjacent insulin monomers may help explain why polyphenolic insulin formulations are able to retain oligomeric R-state insulin structures in aqueous environments lacking excess constituents of an oligomeric insulin formulation (see FIG. 6). Observing the molecular docking of quercetin to hexameric $R_6$ insulin, in approximately the same three-dimensional orientation relative to FIG. 2, from the vantage point of an electrostatic potential map showing surface-exposed acidic residues (red), basic residues (blue), and neutral residues (white), it is clear that polyphenolic insulin bound to flavonoids and other polyphenolic compounds have a distinct $R_6$ hexameric insulin binding pocket to which they bind (see FIG. 3, element 1). Additionally, in accordance with there being two metal ion centers having 3-fold rotational symmetry in one hexameric $R_6$ insulin, and there being three exposed insulin monomer-monomer dimer interfaces per metal ion 3-fold center of rotational symmetry, there are six total polyphenolic binding pockets, three per each of the two 3-fold center of rotational symmetry, within hexameric $R_6$ insulin.

Figure 3:
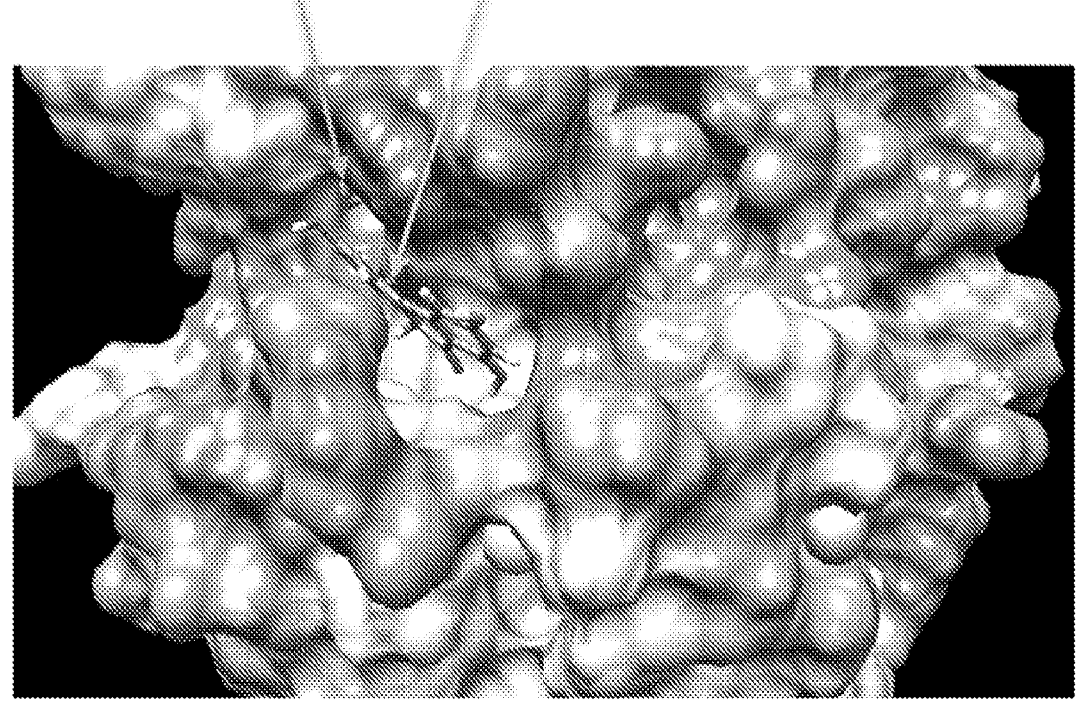
FIG. 3 is an exemplary schematic detail view of a polyphenolic ligand bound to an insulin complex.

It should also be appreciated that in the molecular docking of quercetin to $R_6$ hexameric insulin, from the vantage point of an electrostatic potential map is the placement of resorcinol (see FIG. 3, element 2). From the electrostatic potential map view of quercetin docked to hexameric $R_6$ insulin, resorcinol, which is mostly obscured by surface-exposed residues, is shown deeper within hexameric $R_6$ insulin where it is bound by hydrogen bonds to the A-chain cysteine 6 and A-chain cysteine 11 of a monomeric insulin sub-unit shown in FIG. 2 as the yellow insulin monomeric subunit (FIG. 2, element 6). Quercetin (FIG. 3, element 1) is clearly shown in its own more surface-exposed polyphenolic binding pocket, the location of quercetin situated near the monomer-monomer insulin dimer interface within hexameric $R_6$ insulin. The corresponding hexameric $R_6$ insulin locations in FIG. 2 show insulin monomer one, shown as the blue insulin monomer (FIG. 2, element 4), and insulin monomer two, shown as cyan insulin monomer (FIG. 2, element 5), with quercetin at the top of the monomer-monomer insulin dimer interface of insulin monomer one and insulin monomer two of hexameric $R_6$ insulin.

Figure 4:
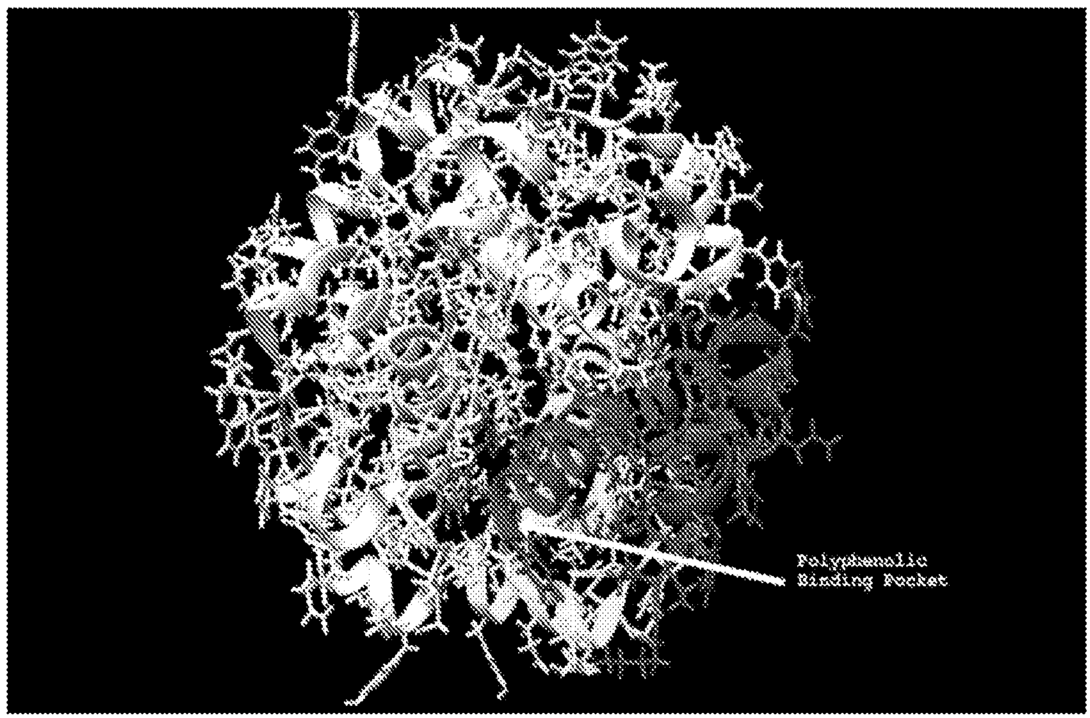
FIG. 4 is an exemplary schematic view of a hexameric insulin complex illustrating the polyphenolic ligand binding pocket.
Figure 5:
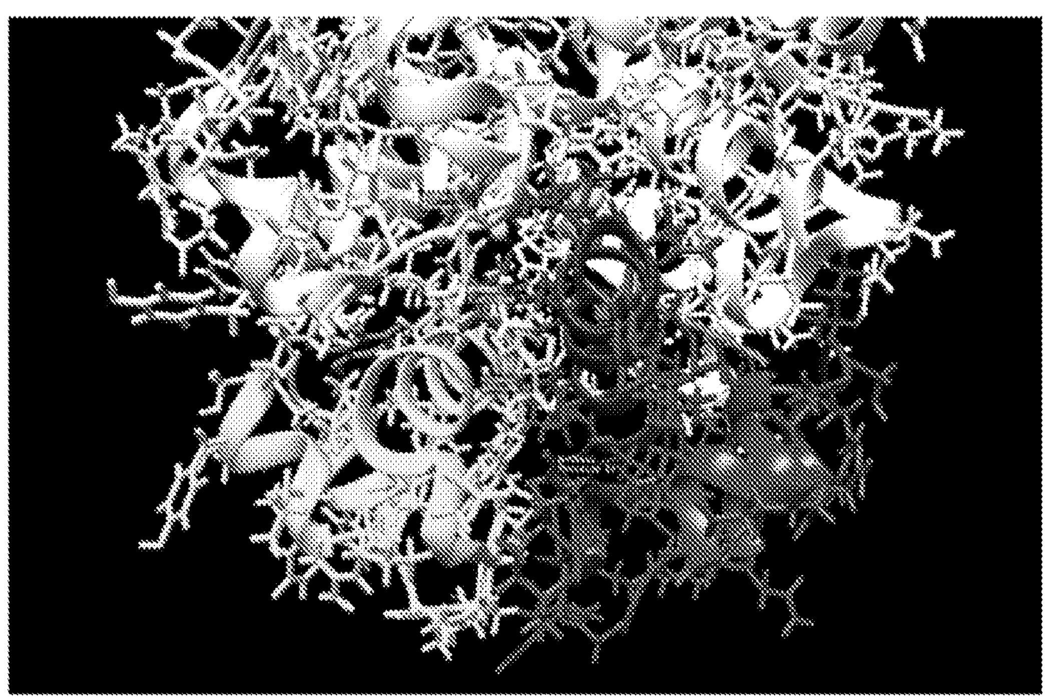
FIGS. 5A and 5B are exemplary schematic detail views of a hexameric insulin complex with polyphenolic ligand binding pocket.
Figure 5:
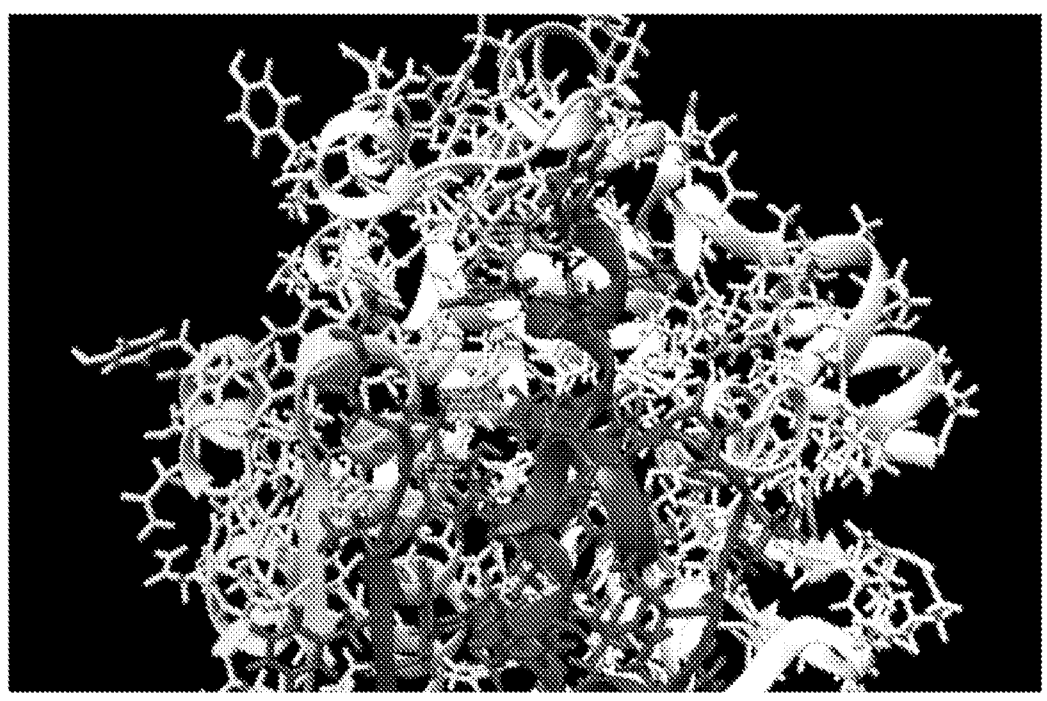

A hybrid ribbon and stick diagram outlining individual amino acid residues in hexameric $R_6$ insulin, shown from a perspective near the center of 3-fold rotational symmetry, can be seen in FIG. 4. Here, the 6 bound resorcinol molecules of hexameric $R_6$ insulin are shown highlighted red and the two zinc ions are shown highlighted green. FIG. 4 shows insulin monomers shown in blue, cyan, and yellow labeled in the same fashion as monomers of the same corresponding colors in FIG. 2 from the vantage point of 3-fold rotational symmetry. The other three insulin monomers within the hexameric $R_6$ insulin depicted in FIG. 4 are shown as white. These white colored insulins are distanced from the particular empty polyphenolic binding pocket emphasized in FIG. 4. As is the case with the small phenolic binding pocket located in proximity to the A-chain of insulin monomers within the dimer-dimer interface of hexameric insulin (FIG. 4, yellow insulin monomer), the adjacent empty polyphenolic binding pocket near the monomer-monomer dimer interface of hexameric insulin is repeated 6 times within hexameric insulin and can be observed 3 times within this hybrid ribbon and stick diagram view of hexameric $R_6$ insulin shown in FIG. 4. A structurally identical polyphenolic binding pocket can be seen with every 120 degree rotation of FIG. 4. The additional structurally identical polyphenolic binding pockets are on the other side of the hexameric $R_6$ insulin and not as easily identified from the side of hexameric $R_6$ insulin shown in FIG. 4, but if viewed would appear in same orientation as polyphenolic binding pockets seen in FIG. 4. Shown in FIG. 5, panel A, is an additional zoomed hybrid ribbon and stick diagram view of the top side of the polyphenolic binding pocket shown without a bound polyphenolic compound. In FIG. 5, panel A, resorcinol and individual amino acid residues that may be important to insulin binding of polyphenolic compounds, but are not necessarily or limited to being important to insulin binding of polyphenolic compounds, are labeled within the hybrid ribbon and stick diagram view: insulin monomer 1, B-chain histidine, at position 5 and tyrosine at position 26; and insulin monomer 2, B-chain tyrosine at position 16. FIG. 5, panel B, shows the same empty polyphenolic binding pocket as shown in FIG. 5, panel A, again shown as a hybrid ribbon and stick diagram, from a side view.

Most long-lasting therapeutic insulin formulations use genetically modified insulin that contains additional amino acids, one or more amino acid substitution not seen in native human insulin amino acid consensus sequence, or a chemical modification designed to reduce the solubility of serum monomeric insulin. Within the present inventive subject matter, long-lasting oligomeric non-genetically modified insulin states are presented that are suitable for pharmaceutical formulations, and that have been produced by addition of a non-toxic and well known compounds (e.g., polyphenolic compound or compounds, metal ions, and small phenolic compounds). Like some kinds of genetically modified insulin designed to create a long-lasting therapeutic insulin, the mechanism of oligomeric insulin stabilization by polyphenolic compounds is likely achieved by stabilizing the insulin monomer-monomer dimer interfaces within the larger hexameric, or other oligomeric, insulin formed by the formulation. Unlike the addition of amino acids or the introduction of non-consensus amino acids to a recombinant human insulin, introduction of a polyphonic compound or compounds to non-genetically modified human insulin pharmaceutical formulations acts, as previously described, to stabilize the monomer-monomer dimer interface of human insulin species by bridging amino acid residues within the monomer-monomer dimer interface of human oligomeric insulin.

Another aspect of this discovery involves the insulin dimer, and therefore monomer stabilizing aspect, of insulin monomer-monomer dimer interface binding compounds including, but not limited to, polyphenolic compounds. Polyphenolic compounds, which may bind to the polyphenolic binding pocket described herein, stabilize serum dimeric insulin and preserve the possibility for future monomeric insulin after a dimeric insulin dissociation event. All species of insulin that have an oligomerization state greater than monomeric insulin have therefore potentially greater stability. By stabilizing any of the oligomeric species of insulin, including dimeric, hexameric, dodecameric, or larger oligomeric insulin with a polyphenolic insulin formulation, in terms of long-lasting insulin efficacy and other insulin types efficacy, the pharmacokinetics and pharmacodynamics of monomeric serum insulin are improved.

Another significant aspect of the inventive subject matter concerns the ability of polyphenolic insulin formulations to increase the biochemical durability of packaged and stored formulated oligomeric insulin species. The stabilization of therapeutic insulin through oligomerization and also crystallization of insulin species is well documented. Pharmaceutical formulations of therapeutic oligomerized insulin greatly reduces fibrillation, denaturation, covalent dimerization, and deamidation of insulin during storage before therapeutic usage. In literature, polyphenols have also been shown to reduce amyloid insulin formation in certain insulin formulations by virtue of the ability of polyphenolic compounds to bind and stabilize monomeric insulin amino acid secondary structure and in doing so prevent monomeric insulin from forming amyloid insulin structures. Prevention of amyloid insulin formation at injection sites of therapeutic insulin may also be facilitated by addition of a polyphenolic compound, or polyphenolic compounds, to therapeutic insulin formulations. Additionally, some polyphenolic compounds have been shown, while the polyphenolic compound is bound to monomeric insulin, to potentiate the ability of polyphenolic-bound monomeric insulin to encounter and bind to a cell surface insulin receptor protein.

Additionally, it has been shown that once a polyphenolic-bound insulin monomer complex binds to an insulin receptor protein, there can be an increase in insulin receptor signal transduction. It has been reported that some polyphenolic compounds can affect binding of insulin receptor proteins by acting to directly bridge monomeric insulin and insulin receptor proteins. Said another way, various polyphenolic compounds have been shown to be simultaneously bound to monomeric insulin and insulin receptors as part of a monomeric insulin-polyphenolic compound insulin receptor complex. Additionally, literature has shown some polyphenolic compounds have the potential to bind to cell surface insulin receptors, alone in the absence of insulin, and affect the uptake of glucose from outside cells. These advantages in increased formulated insulin stability, reduction of amyloid formation, increase in insulin receptor binding events per insulin dosage, and increase in insulin receptor potentiated signal transduction offer additional benefits over other long-lasting therapeutic insulin formulations and other types of insulin formulation in general.

In still further contemplated aspects of the inventive subject matter, the inventors also contemplates that the compounds and compositions presented herein will be suitable to not only reduce blood sugar in a subject in need thereof, but also to concurrently reduce or prevent the accumulation of insulin related and other neurodegenerative amyloid plaque. Similarly, contemplated compounds and compositions may not only be effective in reducing blood glucose but also to concurrently facilitate weight loss in a subject in need thereof. Likewise, contemplated compounds and compositions may not only be effective in reducing blood glucose but also to concurrently reduce formation of advanced glycation end products (AGEs) associated with diabetes, atherosclerosis, chronic kidney disease, Alzheimer's disease and other age-related degenerative diseases in a subject in need thereof.

EXAMPLES

Despite the relatively small molecular weight of insulin, the structure of complexes formed by insulin is fairly dynamic, which has direct physiological consequences. On a monomeric level, the A- and B chains of insulin exhibit extensive secondary structures despite their fairly short lengths. The A chain has two α-helical segments (A1-A8 and A12-A19) that are nearly antiparallel and that are connected by a non-canonical turn (residues A9-A12), bringing into proximity the N- and C-chain termini. The B chain contains central α-helix (residues B9-B19) that is flanked by disulfide bridges (cystines A7-B7 and A20-B19) and β-turns (B7-B10 and B20-B23). Residues B1-B5 are extended in the T state. Each β-turn contains at least one conserved Gly with positive dihedral angle (residues B8, B20, and B23). The B7-B10 β-turn enables the side chain of His B5 to interact with the central region of the A chain in association with cysteine A7-B7. The B20-B23 β-turn orients the C-terminal segment of the B-chain (residues B23-B30) in close proximity and antiparallel to the central B-chain α-helix. Residues B24-B28 have a β-strand structure. The conserved aromatic side chains of Phe B24 and Tyr B26 are in contact with Leu B11, Val B12, and Leu B15 of the central B-chain α-helix, defining an α-turn-supersecondary structure.

Dimerization is observed in insulin complexes. Here, the T6 insulin hexamer contains three dimers in which two insulin molecules form an extensive nonpolar interface. The C-terminal segments of each B-chain come together to form an antiparallel β-sheet (residues B24 -B28 and its dimer-related mates). This sheet, containing four intermolecular main-chain hydrogen bonds, is further stabilized by hydrophobic interactions involving the side chains of Val B12, Tyr B16, Phe B24, Tyr B26, Pro B28, and to some extent, Phe B25. These residues are shielded from contact with solvent (with the exception of Phe B25). Although dimerization is associated with local and non-local damping of conformational fluctuations within the protein (relative to the isolated monomer), an entropic gain is obtained from desolvation of non-polar surfaces, predicted to liberate bound water molecules into the bulk solution. Dimerization does not require zinc ions and exhibits a dissociation constant $K_d$ of approximately $10^{-5}$ M.

Hexamer formation is observed in the presence of $Zn^{2+}$, where insulin dimers associate to form hexameric units coordinated by two zinc ions within the central axis of the hexamer. These axial $Zn^{2+}$ ions are coordinated to the imidazole groups of His B10 (three per zinc ion) and in a particular instance to His B5. In this hexamer three dimers are related by a 3-fold symmetry axis, which is located in the hydrophilic pore at the center of the hexameric unit that connects the two $Zn^{2+}$ ions. Each zinc ion is octahedrally coordinated to three His B10 imidazole nitrogens and three water molecules. The three-fold symmetry axis is perpendicular to the approximate two-fold symmetry axis of the dimers. Contacts between dimers in the hexamer are less extensive than contacts between protomers within the dimer.

Moreover, structural complexity of insulin is even further increased, depending on various additional factors. In crystals and in solution insulin can form three structural families of hexamers (T6, T3Rf3, and R6). The equilibrium between these structures is a function of salt concentration and the binding of phenolic ligands (which favors the R state or frayed Rf state). The T3Rf3 hexamer and R6 hexamer are arranged similarly to the classical T6 hexamer in overall aspects.

T3Rf3 hexamers (also referred to as T3R3 hexamers) of zinc insulin crystals can be induced by high concentrations of sodium chloride. Each dimeric unit consists of one molecule I and one molecule II monomer. Whereas in the hexamer the molecule I trimer (T3) has the same octahedral zinc-ion coordination as in the T6 hexamer, the molecule II trimer (Rf3) exhibits substantial, however, displays structural reorganization. The N-terminal B-chain residues B3-B8 (with "fraying" of flexible terminal residues B1 and B2) forms a continuous extension of the central B9-B19 α-helix. This transition in secondary structure, which entails a movement of more than 25 Å at B1, is coupled to a change in coordination of the second axial zinc ion from octahedral to tetrahedral. The TR transition also causes a rotation of the A1-A8 α-helix (thus requiring a reorganization of the details of side-chain packing in the hydrophobic core and change in conformation of the A7-B7 disulfide bridge) and small displacement of the B24-B28 β-strand away from the A chain, breaking the main-chain hydrogen bond between Phe B25 and Tyr A19. Similar T3Rf3 hexamers may be induced at lower salt concentrations by small phenolic ligands wherein the Rf3 trimer contains three bound phenolic molecules.

High concentrations of phenolic ligands induce a further conformation change to form the R6 hexamer. The hexamer contains six bound small phenolic ligands. Crystal forms exist which exhibit rigorous six-fold symmetry, or which contain six independent protomers in the asymmetric unit with only quasi-six-fold symmetry. In the R6 hexamer each protomer contains a continuous B1-B19 α-helix and breakage of the B25-A19 main-chain hydrogen bond association with a small displacement of the B-chain C-terminus segment from the A chain. The specific binding site for the phenolic ligand does not pre-exist in the T6 structure but may occur in nascent form as part of an extended conformational equilibrium among the three hexamer types. In this R-state-specific binding pocket two hydrogen bonds engage the phenolic hydroxyl group from the A6 carbonyl oxygen and A11 amide hydrogen. The side chain of His B5 packs against each phenolic molecule.

The phenol-stabilized R6 hexamer exhibits augmented thermodynamic and kinetic stability relative to the T6 hexamer. Retarding physical- and chemical degradation of the polypeptide chains, these favorable biophysical properties have been exploited in pharmaceutical formulations to increase the shelf-life of insulin products. Because phenolic ligands were traditionally employed in insulin formulations due to their bacteriostatic properties, their additional role as protein-stabilizing agents and their elegant structural role in the hexamer represents the value of serendipity as a source of therapeutic advance.

The inventor has now discovered that insulin complexes, and especially R6 and possibly $T_3R_3$ complexes, contain a polyphenol ligand binding pocket that is distinct from the small phenolic binding pocket discussed above, and that when occupied by a polyphenol, the polyphenol enables further stabilization of an insulin complex. Viewed from another perspective, the insulin complex can be stabilized with a ligand that binds to at least one (and more typically two) amino acid side chains of an amino acid in a B-chain of a first insulin monomer and to at least one amino acid side chain of another amino acid in a B-chain of a second insulin monomer to thereby increase a binding interaction between the first and second insulin monomers. Importantly, as introduced above, the $T_3R_3$ or $R_6$ conformation of the insulin complex due to interaction with the polyphenol, yet without cross-linking, leads to improved stabilization of the insulin complex while still allowing the monomers of the insulin complex to disassociate for their therapeutic effect.

Depending on insulin monomer types, hexameric $T_3R_3$ or $R_6$ insulin containing a small phenolic compound and a polyphenolic compound may be formed using a variety of conditions, and the following protocol describes exemplary preparations of insulin complexes used for the example formulations presented herein. Insulin monomers more like native insulin having isoelectric point (PI) values between 5.0 and 5.5 are able to form $T_3R_3$ or $R_6$ insulin complexes with the addition of water as a solvent, a buffer having a pH of 7.5 (e.g., 50 mM Tris) a 1:2 molar ratio metal ion salt to insulin (e.g., 0.3 mM cobalt), followed by the addition of molar excess phenol (e.g., 50 mM final concentration from 200 mM stock) phenol (e.g., phenol) added before or concurrently added with a polyphenol in a equimolar amount to insulin (e.g., 0.6 mM added from 50 mM quercetin stock dissolved in 100% ethanol). Concentrations used in creating complex insulin range from 1 to 12 mg/ml (e.g., 3.5 mg/ml, or 0.6 mM). The incubation time for complex formation ranges from one or more hours (e.g., 1-8 hours) to several days. The formation of hexameric $T_3$, $T_3R_3$, or $R_6$ insulin could first be noted after 4 hours post mixture of water, buffer, insulin, metal salt, small phenolic, and polyphenolic compound. After 16 hours $T_3R_3$ or $R_6$ insulin is clearly present as a 574 nm peak becomes visible in elution volumes representative of hexameric insulin containing tetrahedral cobalt ions. It is customary for hexameric or dodecameric insulin complexes to be crystalized, and such complexes remain stable and are used as a crystalline or semicrystalline formulation before administration to a patient.

Because a number of modification have been made to many pharmaceutical forms of insulin and these modification modify the isoelectric point and steric properties of the insulin monomer and subsequently the interactions between monomers and subsequently also the interactions between hexameric species in crystallization, large-scale crystallization conditions will vary with monomer type. It is anticipated larger scale production of $T_3R_3$ or $R_6$ polyphenolic insulin will involve insulin concentrations between 0.01 and 10 mg/ml, metal ions in a range between 0.005 and 1 mg/ml, a range of salt between 0.1 and 0.5 M, small phenolic compounds in a range between 1 and 50 mg/ml, and a polyphenolic compound or compounds in equimolar to 50 fold molar excess to insulin. Temperatures for crystallization of polyphenolic insulin can be estimated to between 2 and 30 Celsius degrees with 2-8 Celsius likely being more favorable. The pH for optimized crystallization will vary between insulin monomer species with a pH rang of 5.9 to 6.2 being more likely native human insulin polyphenolic formulations; insulin monomer species with a more basic PI, such as Glargine may require a pH in the range of 6.3 to 9.5. It is foreseen organic solvents in the range of 10-30 percent by volume may be advantageous for the crystallization of some forms of polyphenolic insulin. Optimized crystallization can be estimated to be in range of hours to several days.

The examples that follow demonstrate the differences in aqueous oligomeric states seen in insulin formulated without the addition of a polyphenolic compound (comparative) and with the addition of a polyphenolic compound (exemplary). Shown in FIG. 6, panel A, is an ultraviolet 280 nm absorbance unit chromatograph from a 10 mm×300 mm size exclusion chromatography column that was injected with a 96 hour incubation of native human insulin, having native consensus amino acid sequence, in a formulation that can induce R-state oligomeric insulin (50 mM Tris pH 7.5, 0.3 mM CoCl2, 50 mM phenol, and 0.6 mM Insulin). The use of $CoCl_2$ as insulin-coordinating metal allows for the differentiation of octahedrally and tetrahedrally coordinated cobalt ions within oligomeric insulin, and therefore for the differentiation of oligomeric R-state insulin that has tetrahedrally coordinated cobalt from T-state insulin that does not have tetrahedrally coordinated cobalt, by means of ultraviolet 574 nm absorbance. The running buffer used, 10 mM Tris, 140 mM NaCl, pH 7.5, run at 1 milliliter per minute, represents a pH and salt concentration that is similar to human physiological conditions; and the running buffer contains no additional component. It should be noted that the running buffers used herein did not contain any additional metal ions or small phenolic compounds.

FIG. 6, panel A, shows insulin in previously described conditions does not form a significant amount of larger species; and instead, the majority of the incubated insulin eluted in a peak seen at 13.62 minutes (marked top of peak), which represents a dimeric insulin species with a significant tailing on the right side, possibly indicative of monomeric insulin. Because there are no larger species shown eluting before 13.62 minutes in the ultraviolet 280 nm absorbance unit chromatograph, there was no need to show ultraviolet 574 nm absorbance chromatograph detecting tetrahedrally coordinated cobalt ions.

Shown in FIG. 6, panel B, is a resulting ultraviolet 280 nm absorbance unit chromatograph from a 10 mm×300 mm size exclusion chromatography column that has been injected with a 96-hour incubation of native consensus amino acid human insulin in a Polyphenolic Insulin formulation that can induce oligomeric R-state insulin (50 mM Tris pH 7.5, 0.3 mM CoCl2, 50 mM phenol, 0.6 mM Insulin and 0.4 mM quercetin). The running buffer used, 10 mM Tris, 140 mM NaCl, pH 7.5, run at 1 milliliter per minute, represents a pH and salt concentration that is similar to human physiological conditions; this buffer contained no additional Polyphenolic Insulin component, and this buffer was the same buffer used in the chromatography shown in FIG. 6, panel A. FIG. 6, panel B clearly shows the existence of larger species: species at 9.98 minutes (marked top of peak) may represent dodecameric R-state insulin; species at 11.27 minutes (marked top of peak) represents hexameric R-state insulin, and smallest peak seen at 13.94 minutes (marked top of peak) represents mostly dimeric insulin, with the right tailing of peak likely being monomeric insulin.

FIG. 6, panel C, shows that the larger chromatographic peaks seen in FIG. 6, panel B, have corresponding peaks eluting at approximately the same time when viewed by ultraviolet 574 nm absorbance, and these peaks do indicate tetrahedrally coordinated cobalt ions. The chromatographic peaks in FIG. 6, panel C, therefore demonstrate the larger chromatographic peaks seen in FIG. 6, panel B, by ultraviolet 280 nm absorbance, represent oligomeric R-state insulin that has retained its oligomeric state in running buffer containing no additional metal ions, small phenolic compounds, or polyphenolic compounds.

In further aspects of the inventive subject matter, the inventor performed docking simulations of a variety of compounds to the apical area of the interface formed by respective B-chains of a first and a second insulin monomer in an insulin complex (polyphenol binding pocket).

A chemical entity can be examined either through visual inspection or using computer modeling by a docking program such as GRAM, DOCK, or AutoDock Vina. These examinations can include computer fitting of chemical entities to a target to ascertain how well the shape and the chemical structure of each chemical entity will complement or interfere with the structure of the subject polypeptide. Computer programs can also be employed to estimate the attraction, repulsion, and steric hindrance of the chemical entity to a druggable region, for example. Generally, the tighter the fit (i.e., the lower the steric hindrance, and/or the greater the attractive force) the more potent the chemical entity will be because these properties are consistent with a tighter binding constant. Furthermore, the more specificity in the design of a chemical entity the more likely that the chemical entity will not interfere with related proteins, which can minimize potential side-effects due to unwanted interactions.

Various polyphenols were examined in Chimera using AutoDock Vina (Trott O, Olson A J. AutoDock Vina: improving the speed and accuracy of docking with a new scoring function, efficient optimization, and multithreading. *J Comput Chem.* 2010; 31 (2): 455-461. doi: 10.1002/jcc.21334, which is incorporated by reference in its entirety) was used for docking studies. Exemplary results are provided in the table below listing selected compounds and their respective binding energies to the polyphenol binding pocket. Total binding energies for all symmetrical monomer-monomer interfaces (6-sites) is also provided. A low (negative) energy indicates a greater binding interaction.

| Compound (ligand) | Smiles | Compound Class | IUPAC | Docking Score (kcal/mol) | Potential Total (6X Binding, kcal/mol) |
|---|---|---|---|---|---|
| Cyanidin | C1=CC(=C(C=C1C2=C(C=C3C(=CC(=CC3=[O+]2)O)O)O)O)O | Anthocyanidin | 2-(3,4-Dihydroxyphenyl)-3,5,7-trihydroxy-1$\lambda^4$-benzopyran-1-ylium | −7.4 | −44.4 |
| Delphinidin | C1=C(C=C(C(=C1O)O)O)C2=C(C=C3C(=CC(=CC3=[O+]2)O)O)O.[Cl−] | Anthocyanidin | 3,5,7-Trihydroxy-2-(3,4,5-trihydroxyphenyl)-1$\lambda^4$-1-benzopyran-1-ylium | −7.6 | −45.6 |
| Delphinidin | C1=C(C=C(C(=C1O)O)O)C2=C(C=C3C(=CC(=CC3=[O+]2)O)O)O.[Cl−] | Anthocyanidin | 3,3',4',5,5',7-Hexahydroxyflavylium | −7.5 | −45 |
| Pelargonidin | C1=CC(=CC=C1C2=C(C=C3C(=CC(=CC3=[O+]2)O)O)O)O | Anthocyanidin | 3,5,7-Trihydroxy-2-(4-hydroxyphenyl)-1$\lambda^4$-benzopyran-4-ylium | −7.4 | −44.4 |
| Peonidin | Oc1cc2c(O)cc(O)cc2[o+]c1c3cc(OC)c(O)cc3 | Anthocyanidin | 3,5,7-Trihydroxy-2-(4-hydroxy-3-methoxyphenyl)-1$\lambda^4$-benzopyran-1-ylium | −7.2 | −43.2 |
| Malvidin | Oc1cc2c(O)cc(O)cc2[o+]c1c3cc(OC)c(O)c(OC)c3 | Anthocyanidin | 3,5,7-Trihydroxy-2-(4-hydroxy-3,5-dimethoxy)-1$\lambda^4$-benzopyran-1-ylium | −7.4 | −44.4 |
| Petunidin | Oc1cc2c(O)cc(O)cc2[o+]c1c3cc(O)c(O)c(OC)c3 | Anthocyanidin | 2-(3,4-Dihydroxy-5-methoxyphenyl)-3,5,7-trihydroxy-1$\lambda^4$-benzopyran-1-ylium | −7.6 | −45.6 |
| Chrysanthemin | [Cl−].O(c1c([o+]c2c(c1)c(O)cc(O)c2)c3ccc(O)c(O)c3)[C@@H]4O[C@@H]([C@@H](O)[C@H](O)[C@H]4O)CO | Anthocyanin | (2S,3R,45,5S,6R)-2-[2-(3,4-dihydroxyphenyl)-5,7-dihydroxychromenylium-3-yl]oxy-6-(hydroxymethyl)oxane-3,4,5-triol chloride | −7.5 | −45 |
| Cyanidin-3,5-O-diglucoside | c1cc(c(cc1c2c(cc3c([o+]2)cc(cc3O[C@H]4[C@@H]([C@H]([C@@H]([C@H](O4)CO)O)O)O)O[C@H]5[C@@H]([C@H]([C@@H]([C@H](O5)CO)O)O)O)O)O | Anthocyanin | Cyanidin-3,5-O-diglucoside | −8.4 | −50.4 |
| Malvidin glucoside-ethyl-catechin | CC(c1c2[o+]c(c(cc2c(O)cc1O)O[C@@H]1O[C@H](CO)[c@@H](O)[C@H](O)[C@H]1O)-c1cc(OC)c(O)c(c1)OC)c1c2OC(C(O)Cc2c(O)cc1O)c1cc(O)c(O)cc1 | Anthocyanin | 8-{(1E)-1-[(2R*,3S*)-2-(3,4-Dihydroxyphenyl)-3,5,7-trihydroxy-3,4-dihydro-2H-1-benzopyran-8-yl]ethyl}-5,7-dihydroxy-2-(4-hydroxy-3,5-dimethoxyphenyl)-3-{[(2S,3R,4S,5S,6R)-3,4,5-trihydroxy-6-(hydroxymethyl)oxan-2-yl]oxy}-1$\lambda^4$-benzopyran-1-ylium | −7.7 | −46.2 |

-continued

| Compound (ligand) | Smiles | Compound Class | IUPAC | Docking Score (kcal/mol) | Potential Total (6X Binding, kcal/mol) |
|---|---|---|---|---|---|
| Malvidin-3-O-(6-p-coumaroyl)glucoside | O[C@@H]4[C@@H](O)[C@H](O)[C@@H](OC2═CC═1C(O)═CC(O)═CC═1[O+]═C2C3═CC(OC)═C(O)C(═C3)OC)O[C@H]4COC(═O)/C═C/C5═CC═C(O)C═C5 | Anthocyanin | (42R,43S,44R,45R,46S,8E)-14,25,27,43,44,45,104-Heptahydroxy-13,15-dimethoxy-7-oxo-1λ$^4$-3,6-dioxa-2(2,3)-[1]benzopyrana-4(2,6)-oxana-1,10(1)-dibenzenadecaphan-8-en-21-ylium | −8.4 | −50.4 |
| Myrtillin | C1═C(C═C(C(═C1O)O)O)C2═C(C═C3C(═CC(═CC3═[O+]2)O)O)OC4C(C(C(C(O4)CO)O)O)O.[Cl−] | Anthocyanin | (2S,3R,4S,5S,6R)-2-[5,7-dihydroxy-2-(3,4,5-trihydroxyphenyl)chromenylium-3-yl]oxy-6-(hydroxymethyl)oxane-3,4,5-triol chloride | −7.2 | −43.2 |
| Oenin | COC1═CC(═CC(═C1O)OC)C2═C(C═C3C(═CC(═CC3═[O+]2)O)O)OC4C(C(C(C(O4)CO)O)O)O | Anthocyanin | 5,7-Dihydroxy-2-(4-hydroxy-3,5-dimethoxyphenyl)-3-{[(2S,3R,4S,5S,6R)-3,4,5-trihydroxy-6-(hydroxymethyl)oxan-2-yl]oxy}-1λ$^4$-benzopyran-1-ylium | −7.1 | −42.6 |
| Oxovitisin A | COC1═CC(═CC(═C1O)OC)C2═C(C3═C4C(═O)CC(═O)C═C4O2)OC(═C3)O[C@H]5[C@@H]([C@H]([C@@H]([C@H](O5)CO)O)O)O | Anthocyanin | 7-hydroxy-3-(4-hydroxy-3,5-dimethoxyphenyl)-4-[(2S,3R,4S,5S,6R)-3,4,5-trihydroxy-6-(hydroxymethyl)oxan-2-yl]oxy-2,8-dioxatricyclo[7.3.1.05,13]trideca-1(12),3,5(13),6,9-pentaen-11-one | −8.2 | −49.2 |
| Pelargonin | c1cc(ccc1c2c(cc3c([o+]2)cc(cc3O[C@H]4[C@@H]([C@H]([C@@H]([C@H](O4)CO)O)O)O)O)O[C@H]5[C@@H]([C@H]([C@@H][C@H](O5)CO)O)O)O)O | Anthocyanin | 7-Hydroxy-2-(4-hydroxyphenyl)-3,5-bis{[(2S,3R,4S,5S,6R)-3,4,5-trihydroxy-6-(hydroxymethyl)oxan-2-yl]oxy}-1λ$^4$-benzopyran-1-ylium | −8.3 | −49.8 |
| Peonidin-3-O-glucoside | COC1═C(C═CC(═C1)C2═C(C═C3C(═CC(═CC3═[O+]2)O)O)OC4C(C(C(C(O4)CO)O)O)O)O | Anthocyanin | 5,7-Dihydroxy-2-(4-hydroxy-3-methoxyphenyl)-3-{[(2S,3R,4S,5S,6R)-3,4,5-trihydroxy-6-(hydroxymethyl)oxan-2-yl]oxy}-1λ$^4$-benzopyran-1-ylium | −7.9 | −47.4 |
| Pinotin A | COc1cc(cc(c1O)OC)c2c(c3c4c([o+]2)cc(cc4OC(═C3)c5ccc(c(c5)O)O)O)O[C@H]6[C@@H]([C@H]([C@@H]([C@H](O6)CO)O)O)O | Anthocyanin | [7-(3,4-dihydroxyphenyl)-3-(4-hydroxy-3,5-dimethoxyphenyl)-4-[(2S,3R,45,5S,6R)-3,4,5-trihydroxy-6-(hydroxymethyl)oxan-2-yl]oxy-2,8-dioxatricyclo[7.3.1.05,13]trideca-1(12),3,5(13),6,9-pentaen-11-ylidene]oxidanium | −8.2 | −49.2 |
| Vitisin A (pyranoanthocyanin) | O═CC1═C2C3═C(OC1═O)C═C(O)C═C3[O+]([H])C(C4═CC(OC)═C(O)C(OC)═C4)═C2O[C@@H]5O[C@H](CO)[C@@H](O)[C@H](O)[C@H]5O | Anthocyanin | 3-Formyl-8-hydroxy-5-(4-hydroxy-3,5-dimethoxyphenyl)-2-oxo-4-{[(2S,3R,45,5S,6R)-3,4,5-trihydroxy-6-(hydroxymethyl)oxan-2-yl]oxy}-2H-pyrano[4,3,2-de][1]benzopyran-6-ium | −7 | −42 |

-continued

| Compound (ligand) | Smiles | Compound Class | IUPAC | Docking Score (kcal/mol) | Potential Total (6X Binding, kcal/mol) |
|---|---|---|---|---|---|
| Vitisin B (pyranoanthocyanin) | COc1cc(cc(c1O)OC)c2c(c3c4c([o+]2)cc(cc4OC=C3)O)O[C@H]5[C@@H]([C@H]([C@@H]([C@H](O5)CO)O)O)O | Anthocyanin | 8-Hydroxy-2-(4-hydroxy-3,5-dimethoxyphenyl)-3-{[(2S,3R,4S,5S,6R)-3,4,5-trihydroxy-6-(hydroxymethyl)oxan-2-yl]oxy}-1λ$^4$-pyrano[4,3,2-de][1]benzopyran-1-ylium | −7.6 | −45.6 |
| Malvin | COC1=CC(=CC(=C1O)OC)C2=C(C=C3C(=CC(=CC3=[O+]2)O)O[C@H]4[C@@H]([C@H]([C@@H]([C@H](O4)CO)O)O)O)O[C@H]5[C@@H]([C@H]([C@@H]([C@H](O5)CO)O)O)O | Anthocyanin glucoside | 7-Hydroxy-2-(4-hydroxy-3,5-dimethoxyphenyl)-3,5-bis{[(2S,3R,4S,5S,6R)-3,4,5-trihydroxy-6-(hydroxymethyl)oxan-2-yl]oxy}-1λ$^4$-benzopyran-1-ylium | −8.3 | −49.8 |
| Ethyl caffeate | CCOC(=O)/C=C/C1=CC(=C(C=C1)O)O | Aromatic acid | Ethyl (2E)-3-(3,4-dihydroxyphenyl)prop-2-enoate | −6 | −36 |
| Fertaric acid | Oc1ccc(cc1OC)/C=C/C(=O)OC(C(=O)O)C(O)C(=O)O | Aromatic acid | 2-Hydroxy-3-{[(2E)-3-(4-hydroxy-3methoxyphenyl)prop-2-enoyl]oxy}butandioic acid | −6.5 | −39 |
| Ferulic acid | COc1cc(ccc1O)/C=C/C(=O)O | Aromatic acid | (2E)-3-(4-hydroxy-3-methoxyphenyl)prop-2-enoic acid | −6.5 | −39 |
| Phyllodulcinol | COc1ccc([C@@H]2Cc3cccc(O)c3C(=O)O2)cc1O | Coumarin | 5,7-Dihydroxy-2-phenyl-2,3-dihydro-4H-chromen-4-one | −7.8 | −46.8 |
| Coumestan | C1=CC=C2C(=C1)C3=C(O2)C4=CC=CC=C4OC3=O | Coumestan | [1]benzofuro[3,2-c]chromen-6-one | −8 | −48 |
| Coumestrol | C1=CC2=C(C=C1O)OC3=C2C(=O)OC4=C3C=CC(=C4)O | Coumestan | 3,9-Dihydroxy-6H-[1]benzofuro[3,2-c][1]benzopyran-6-one | −7.7 | −46.2 |
| Plicadin | Oc4cc5oc2c(C(=O)Oc1c3C=CC(C)(C)Oc3ccc12)c5cc4 | Coumestan | 9-Hydroxy-2,2-dimethyl-2H,6H-([1]benzofuro[2,3-d']benzo[1,2-b:3,4-b']dipyran)-6-one | −9.5 | −57 |
| Wedelolactone | O=C3Oc4cc(OC)cc(O)c4c2oc1c(cc(O)c(O)c1)c23 | Coumestan | 1,8,9-Trihydroxy-3-methoxy-6H-[1]benzofuro[3,2-c][1]benzopyran-6-one | −7.7 | −46.2 |
| Bisdemethoxy-curcumin | C1=CC(=CC=C1C=CC(=O)CC(=O)C=CC2=CC=C(C=C2)O)O | Curcuminoid | (1E,6E)-1,7-bis(4-hydroxyphenyl)hepta-1,6-diene-3,5-dione | −7.5 | |
| Curcumin glucuronide | COC1=C(C=CC(=C1)C=CC(=O)CC(=O)C=CC2=CC(=C(C=C2)OC3C(C(C(C(O3)C(=O)O)O)O)O)OC)O | Curcuminoid metabolite | (2S,3S,4S,5R,6S)-3,4,5-trihydroxy-6-[4-[(1E,6E)-7-(4-hydroxy-3-methoxyphenyl)-3,5-dioxohepta-1,6-dienyl]-2-methoxyphenoxy]oxane-2-carboxylic acid | −8.5 | −51 |
| Curcumin sulfate | COC1=C(C=CC(=C1)C=CC(=O)CC(=O)C=CC2=CC(=C(C=C2)OS(=O)(=O)O)OC)O | Curcuminoid metabolite | [4-[(1E,6E)-7-(4-hydroxy-3-methoxyphenyl)-3,5-dioxohepta-1,6-dienyl]-2-methoxyphenyl] hydrogen sulfate | −7.6 | −45.6 |
| Dihydrocurcumin | COC1=C(C=CC(=C1)CCC(=O)CC(=O)C=CC2=CC(=C(C=C2)O)OC)O | Curcuminoid metabolite | (E)-1,7-bis(4-hydroxy-3-methoxyphenyl)hept-1-ene-3,5-dione | 6.9 | 41.4 |
| Hexahydrocur-cumin | COC1=C(C=CC(=C1)CCC(CC(=O)CCC2=CC(=C(C=C2)O)OC)O)O | Curcuminoid metabolite | 5-hydroxy-1,7-bis(4-hydroxy-3-methoxyphenyl)heptan-3-one | −5.8 | −34.8 |

-continued

| Compound (ligand) | Smiles | Compound Class | IUPAC | Docking Score (kcal/mol) | Potential Total (6X Binding, kcal/mol) |
|---|---|---|---|---|---|
| Octahydrocurcumin | COC1=C(C=CC(=C1)CCC(CC(CCC2=CC(=C(C=C2)O)OC)O)O)O | Curcuminoid metabolite | 1,7-bis(4-hydroxy-3-methoxyphenyl)heptane-3,5-diol | −6.2 | −37.2 |
| Tetrahydrocurcumin | COC1=C(C=CC(=C1)CCC(=O)CC(=O)CCC2=CC(=C(C=C2)O)OC)O | Curcuminoid metabolite | 1,7-bis(4-hydroxy-3-methoxyphenyl)heptane-3,5-dione | −6 | −36 |
| Demethoxycurcumin | COC1=C(C=CC(=C1)C=CC(=O)CC(=O)C=CC2=CC=C(C=C2)O)O | Curcuminoid | (1E,6E)-1-(4-hydroxy-3-methoxyphenyl)-7-(4-hydroxyphenyl)hepta-1,6-diene-3,5-dione | −7.4 | −44.4 |
| Enterodiol | C1=CC(=CC(=C1)O)C[C@@H](CO)[C@@H](CC2=CC(=CC=C2)O)CO | Enterolignan | (2R,3R)-2,3-Bis[(3-hydroxyphenyl)methyl]butane-1,4-diol | −5.8 | −34.8 |
| Enterolactone | C1[C@@H]([C@H](C(=O)O1)CC2=CC(=CC=C2)O)CC3=CC(=CC=C3)O | Enterolignan | (3R,4R)-3,4-Bis [(4-hydroxyphenyl)methyl]oxolan-2-one | −7.4 | −44.4 |
| Lariciresinol | COc1cc(ccc1O)C[C@H]2CO[C@@H]([C@H]2CO)c3ccc(c(c3)OC)O | Enterolignan | 4-[(2S,3R,4R)-4-[(4-hydroxy-3-methoxyphenyl)methyl]-3-(hydroxymethyl)oxolan-2-yl]-2-methoxyphenol | −7.3 | −43.8 |
| Matairesinol | O=C2OC[C@H](Cc1cc(OC)c(O)cc1)[C@H]2Cc3ccc(O)c(OC)c3 | Enterolignan | (3R,4R)-3,4-Bis [(4-hydroxy-3-methoxyphenyl)methyl]oxolan-2-one | −7.2 | −43.2 |
| Leucocianidol | C1=CC(=C(C=C1C2C(C(C3=C(C=C(C=C3O2)O)O)O)O)O)O | Flavan-3,4-diol | 2-(3,4-dihydroxyphenyl)-3,4-dihydro-2H-chromene-3,4,5,7-tetrol | −7.2 | −43.2 |
| Apiforol | C1C(C2=C(C=C(C=C2OC1C3=CC=C(C=C3)O)O)O)O | Flavan-4-ol | (2S)-2-(4-hydroxyphenyl)-3,4-dihydro-2H-chromene-4,5,7-triol | −7.4 | −44.4 |
| Luteoforol | C1C(C2=C(C=C(C=C2OC1C3=CC(=C(C=C3)O)O)O)O)O | Flavan-4-ol | 2-(3,4-dihydroxyphenyl)-3,4-dihydro-2H-chromene-4,5,7-triol | −7.6 | −45.6 |
| Afzelechin | C1C(C(OC2=CC(=CC(=C21)O)O)C3=CC=C(C=C3)O)O | Flavanol | (2R,3S)-2-(4-hydroxyphenyl)-3,4-dihydro-2H-chromene-3,5,7-triol | −7 | −42 |
| Epicatechin gallate | O=C(O[C@@H]2Cc3c(O[c@@H]2c1ccc(O)c(O)c1)cc(O)cc3O)c4cc(O)c(O)c(O)c4 | Flavanol | (2R,3R)-2-(3,4-Dihydroxyphenyl)-5,7-dihydroxy-3,4-dihydro-2H-1-benzopyran-3-yl 3,4,5-trihydroxybenzoate | −8.7 | −52.2 |
| Fisetinidol | Oc(c3)cc(O1)c(c3)CC(O)C1c(c2)cc(O)c(O)c2 | Flavanol | (2R,3S)-2-(3,4-Dihydroxyphenyl)-3,4-dihydro-2H-1-benzopyran-3,7-diol | −7.4 | −44.4 |
| Gallocatechol | C1C(C(OC2=CC(=CC(=C21)O)O)C3=CC(=C(C(=C3)O)O)O)O | Flavanol | (2R,3S)-2-(3,4,5-trihydroxyphenyl)-3,4-dihydro-2H-chromene-3,5,7-triol | −7.8 | −46.8 |
| Gallocatechol | C1[C@@H]([C@H](OC2=CC(=CC(=C21)O)O)C3=CC(=C(C(=C3)O)O)O)O | Flavanol | (2R,3S)-2-(3,4,5-trihydroxyphenyl)-3,4-dihydro-2H-chromene-3,5,7-triol | −7.1 | −42.6 |
| Guibourtinidol | Oc1ccc(cc1)[C@H]3Oc2cc(O)ccc2C[C@@H]3O | Flavanol | (2R,3S)-2-(4-Hydroxyphenyl)-3,4-dihydro-2H-1-benzopyran-2,7-diol | −7.5 | −45 |
| Mesquitol | Oc1ccc(cc1O)[C@H]3Oc2c(O)c(O)ccc2C[C@@H]3O | Flavanol | (2R,3S)-2-(3,4-Dihydroxyphenyl)-3,4-dihydro-2H-1-benzopyran-3,7,8-triol | −7.5 | −45 |
| Robinetinidol | C1[C@@H]([C@H](OC2=C1C=CC(=C2)O)C3=CC(=C(C(=C3)O)O)O)O | Flavanol | 5-[(2R,3S)-3,7-Dihydroxy-3,4-dihydro-2H-1-benzopyran-2-yl]benzene-1,2,3-triol | −7.4 | −44.4 |

-continued

| Compound (ligand) | Smiles | Compound Class | IUPAC | Docking Score (kcal/mol) | Potential Total (6X Binding, kcal/mol) |
|---|---|---|---|---|---|
| Catechin-5-O-glucoside | OC[C@H]1O[C@@H](OC2═C3C[C@H](O)[C@H](OC3═CC(O)═C2)C2═CC═C(O)C(O)═C2)[C@H](O)[C@@H](O)[C@@H]1O | Flavanol glucoside | (2S,3R,4S,5S,6R)-2-{[(2R,3S)-2-(3,4-Dihydroxyphenyl)-3,7-dihydroxydihydro-2H-1-benzopyran-5-yl]oxy}-6-(hydroxymethyl)oxane-3,4,5-triol | −8.2 | −49.2 |
| Catechin-7-O-glucoside | O(c2cc3O[C@H](c1ccc(O)c(O)c1)[C@@H](O)Cc3c(O)c2)[C@@H]4O[C@@H]([C@@H](O)[C@H](O)[C@H]4O)CO | Flavanol glucoside | (2S,45,5S)-2-[[(2R,3S)-2-(3,4-Dihydroxyphenyl)-3,5-dihydroxy-3,4-dihydro-2H-chromen-7-yl]oxy]-6-(hydroxymethyl)oxane-3,4,5-triol | −8.2 | −49.2 |
| Eriodictyol | O═C2c3c(O[C@H](c1ccc(O)c(O)c1)C2)cc(O)cc3O | Flavanone | (2S)-2-(3,4-Dihydroxyphenyl)-5,7-dihydroxy-2,3-dihydro-4H-1-benzopyran-4-one | −7.6 | −45.6 |
| Hesperetin | O═C2c3c(O[C@H](c1ccc(OC)c(O)c1)C2)cc(O)cc3O | Flavanone | (2S)-5,7-Dihydroxy-2-(3-hydroxy-4-methoxyphenyl)-2,3-dihydro-4H-1-benzopyran-4-one | −7.7 | −46.2 |
| Liquiritigenin | O═C2c3c(O[C@H](c1ccc(O)cc1)C2)cc(O)cc3 | Flavanone | (2S)-7-Hydroxy-2-(4-hydroxyphenyl)-2,3-dihydro-4H-1-benzopyran-4-one | −7.6 | −45.6 |
| Naringenin | O═C2c3c(O[C@H](c1ccc(O)cc1)C2)cc(O)cc3O | Flavanone | (2S)-5,7-Dihydroxy-2-(4-hydroxyphenyl)-2,3-dihydro-4H-1-benzopyran-4-one | −7.6 | −45.6 |
| Pinocembrin | O═C2c3c(OC(c1ccccc1)C2)cc(O)cc3O | Flavanone | 5,7-Dihydroxy-2-phenyl-2,3-dihydro-4H-chromen-4-one | −7.4 | −44.4 |
| Sterubin | O═C2c3c(O[C@H](c1ccc(O)c(O)c1)C2)cc(OC)cc3O | Flavanone | (2S)-2-(3,4-Dihydroxyphenyl)-5-hydroxy-7-methoxy-2,3-dihydro-4H-1-benzopyran-4-one | −7.6 | −45.6 |
| Hesperidin | O═C4c5c(O)cc(O[C@@H]2O[C@H](CO[C@@H]1O[C@H]([C@H](O)[C@@H](O)[C@H]1O)C)[C@@H](O)[C@H](O)[C@H]2O)cc5O[C@H](c3ccc(OC)c(O)c3)C4 | Flavanone glycoside | (22S,42S,43R,44S,45S,46R,72R,73R,74R,75R,76S)-13,25,43,44,45,73,74,75-Octahydroxy-14-methoxy-76-methyl-22,23-dihydro-24H-3,6-dioxa-2(2,7)-[1]benzopyrana-4(2,6),7(2)-bis(oxana)-1(1)-benzenaheptaphan-24-one | −8.6 | −51.6 |
| Engeletin | CC1C(C(C(C(O1)OC2C(OC3═CC(═CC(═C3C2═O)O)O)C4═CC═C(C═C4)O)O)O)O | Flavanonol | (2R,3R)-5,7-Dihydroxy-2-(4-hydroxyphenyl)-3-{[(2S,3R,4R,5R,6S)-3,4,5-trihydroxy-6-methyloxan-2-yl]oxy}-4H-1-benzopyran-4-one | −7.6 | −45.6 |
| Myricetin 3'-glucoside | C1═C(C═C(C(═C1O)O)OC2C(C(C(C(O2)CO)O)O)O)C3═C(C(═O)C4═C(C═C(C═C4O3)O)O)O | Flavone glucoside | 2-[3,4-dihydroxy-5-[3,4,5-trihydroxy-6-(hydroxymethyl)oxan-2-yl]oxyphenyl]-3,5,7-trihydroxychromen-4-one | −8.6 | −51.6 |
| 6-Hydroxyluteolin | C1═CC(═C(C═C1C2═CC(═O)C3═C(O2)C═C(C(═C3O)O)O)O)O | Flavone | 2-(3,4-dihydroxyphenyl)-5,6,7-trihydroxychromen-4-one | −7.7 | −46.2 |
| Acacetin | COC1═CC═C(C═C1)C2═CC(═O)C3═C(C═C(C═C3O2)O)O | Flavone | 5,7-Dihydroxy-2-(4-methoxyphenyl)-4H-1-benzopyran-4-one | −7.8 | −46.8 |
| Acerosin | COC1═C(C═C(C═C1)C2═CC(═O)C3═C(C(═C(C(═C3O2)OC)O)OC)O)O | Flavone | 5,7-dihydroxy-2-(3-hydroxy-4-methoxyphenyl)-6,8-dimethoxychromen-4-one | −7.5 | −45 |

-continued

| Compound (ligand) | Smiles | Compound Class | IUPAC | Docking Score (kcal/mol) | Potential Total (6X Binding, kcal/mol) |
|---|---|---|---|---|---|
| Alnetin | COC1═C(C(═C2C(═C1O)C(═O)C═C(O2)C3═CC═CC═C3)OC)OCO═ | Flavone | 5-hydroxy-6,7,8-trimethoxy-2-phenylchromen-4-one | −7.2 | −43.2 |
| Apigenin | C\1c3c(O/C(═C/1)c2ccc(O)cc2)cc(O)cc3O | Flavone | 5,7-Dihydroxy-2-(4-hydroxyphenyl)-4H-1-benzopyran-4-one | −7.6 | −45.6 |
| Artocarpetin | COC1═CC(═C2C(═C1)OC(═CC2═O)C3═C(C═C(C═C3)O)O)O | Flavone | 2-(2,4-dihydroxyphenyl)-5-hydroxy-7-methoxychromen-4-one | −7.4 | −44.4 |
| Baicalein | O═C\1c3c(O)c(O)c(O)cc3O/C(═C/1)c2ccccc2 | Flavone | 5,6,7-Trihydroxy-2-phenyl-4H-1-benzopyran-4-one | −7.5 | −45 |
| Cerrosillin | COC1═C(C2═C(C═C1)OC(═CC2═O)C3═CC(═CC(═C3)OC)oc)OC | Flavone | 2-(3,5-dimethoxyphenyl)-5,6-dimethoxychromen-4-one | −7.8 | −46.8 |
| Chrysin | O═C\1c3c(O/C(═C/1)c2ccccc2)cc(O)cc3O | Flavone | 5,7-Dihydroxy-2-phenyl-4H-1-benzopyran-4-one | −7.8 | −46.8 |
| Chrysoeriol | COC1═C(C═CC(═C1)C2═CC(═O)C3═C(C═C(C═C3O2)O)O)O | Flavone | 5,7-Dihydroxy-2-(4-hydroxy-3-methoxyphenyl)-4H-1-benzopyran-4-one | −7.9 | −47.4 |
| Cirsilineol | COC1═C(C═CC(═C1)C2═CC(═O)C3═C(C(═C(C═C3O2)OC)OC)O)O | Flavone | 5-Hydroxy-2-(4-hydroxy-3-methoxyphenyl)-6,7-dimethoxy-4H-1-benzopyran-4-one | −7.5 | −45 |
| Cirsiliol | COC1═C(C(═C2C(═C1)OC(═CC2═O)C3═CC(═C(C═C3)O)O)O)OC | Flavone | 2-(3,4-dihydroxyphenyl)-5-hydroxy-6,7-dimethoxychromen-4-one | −7.6 | −45.6 |
| Cirsimaritin | COC1═C(C(═C2C(═C1)OC(═CC2═O)C3═CC═C(C═C3)O)O)OC | Flavone | 5-hydroxy-2-(4-hydroxyphenyl)-6,7-dimethoxychromen-4-one | −7.4 | −44.4 |
| Corymbosin | COC1═CC(═C2C(═C1)OC(═CC2═O)C3═CC(═C(C(═C3)OC)OC)OC)O | Flavone | 5-hydroxy-7-methoxy-2-(3,4,5-trimethoxyphenyl)chromen-4-one | −7.5 | −45 |
| Diosmetin | COC1═C(C═C(C═C1)C2═CC(═O)C3═C(C═C(C═C3O2)O)O)O | Flavone | 5,7-Dihydroxy-2-(3-hydroxy-4-methoxyphenyl)-4H-benzopyran-4-one | −7.9 | −47.4 |
| Echioidinin | COC1═CC(═C2C(═C1)OC(═CC2═O)C3═CC═CC═C3O)O | Flavone | 5-hydroxy-2-(2-hydroxyphenyl)-7-methoxychromen-4-one | −7.6 | −45.6 |
| Eupatilin | O═C\1c3c(O)c(OC)c(O)cc3O/C(═C/1)c2ccc(OC)c(OC)c2 | Flavone | 2-(3,4-Dimethoxyphenyl)-5,7-dihydroxy-6-methoxychromen-4-one | −7.7 | −46.2 |
| Eupatorin | COC1═C(C═C(C═C1)C2═CC(═O)C3═C(C(═C(C═C3O2)OC)OC)O)O | Flavone | 5-hydroxy-2-(3-hydroxy-4-methoxyphenyl)-6,7-dimethoxychromen-4-one | −7.8 | −46.8 |
| Gardenin D | COC1═C(C═C(C═C1)C2═CC(═O)C3═C(C(═C(C(═C3O2)OC)OC)OC)O)O | Flavone | 5-hydroxy-2-(3-hydroxy-4-methoxyphenyl)-6,7,8-trimethoxychromen-4-one | −7.6 | −45.6 |
| Genkwanin | COC1═CC(═C2C(═C1)OC(═CC2═O)C3═CC═C(C═C3)O)O | Flavone | 5-Hydroxy-2-(4-hydroxyphenyl)-7-methoxy-4H-1-benzopyran-4-one | −7.6 | −45.6 |
| Geraldone | COC1═C(C═CC(═C1)C2═CC(═O)C3═C(O2)C═C(C═C3)O)O | Flavone | 7-hydroxy-2-(4-hydroxy-3-methoxyphenyl)chromen-4-one | −7.6 | −45.6 |
| Hispidulin | COc1c(O)cc2oc(cc(═O)c2c1O)-c1ccc(O)cc1 | Flavone | 5,7-Dihydroxy-2-(4-hydroxyphenyl)-6-methoxy-4H-1-benzopyran-4-one | −7.4 | −44.4 |

-continued

| Compound (ligand) | Smiles | Compound Class | IUPAC | Docking Score (kcal/mol) | Potential Total (6X Binding, kcal/mol) |
|---|---|---|---|---|---|
| Hymenoxin | COC1=C(C=C(C=C1)C2=CC(=O)C3=C(C(=C(C(=C3O2)OC)O)Oc)O)OC | Flavone | 2-(3,4-dimethoxyphenyl)-5,7-dihydroxy-6,8-dimethoxychromen-4-one | −7.5 | −45 |
| Hypolaetin | C1=CC(=C(C=C1C2=CC(=O)C3=C(O2)C(=C(C=C3O)O)O)O)O | Flavone | 2-(3,4-Dihydroxyphenyl)-5,7,8-trihydroxy-4H-1-benzopyran-4-one | −7.7 | −46.2 |
| Isoscutellarein | C1=CC(=CC=C1C2=CC(=O)C3=C(O2)C(=C(C=C3O)O)O)O | Flavone | 5,7,8-Trihydroxy-2-(4-hydroxyphenyl)-4H-1-benzopyran-4-one | −7.7 | −46.2 |
| Jaceosidin | COC1=C(C=CC(=C1)C2=CC(=O)C3=C(O2)C=C(C(=C3O)OC)O)O | Flavone | 5,7-dihydroxy-2-(4-hydroxy-3-methoxyphenyl)-6-methoxychromen-4-one | −7.6 | −45.6 |
| Luteolin | C1=CC(=C(C=C1C2=CC(=O)C3=C(C=C(C=C3O2)O)O)O)O | Flavone | 2-(3,4-Dihydroxyphenyl)-5,7-dihydroxy-4H-1-benzopyran-4-one | −6.8 | −40.8 |
| Mikanin | COC1=CC=C(C=C1)C2=C(C(=O)C3=C(C(=C(C=C3O2)OC)OC)O)O | Flavone | 3,5-dihydroxy-6,7-dimethoxy-2-(4-methoxyphenyl)chromen-4-one | −7.5 | −45 |
| Negletein | COC1=C(C(=C2C(=C1)OC(=CC2=O)C3=CC=CC=C3)O)O | Flavone | 5,6-dihydroxy-7-methoxy-2-phenylchromen-4-one | −7.4 | −44.4 |
| Nepetin | COC1=C(C2=C(C=C1O)OC(=CC2=O)C3=CC(=C(C=C3)O)O)O | Flavone | 2-(3,4-Dihydroxyphenyl)-5,7-dihydroxy-6-methoxy-4H-1-benzopyran-4-one | −7.7 | −46.2 |
| Nevadensin | COC1=CC=C(C=C1)C2=CC(=O)C3=C(C(=C(C(=C3O2)OC)O)OC)O | Flavone | 5,7-dihydroxy-6,8-dimethoxy-2-(4-methoxyphenyl)chromen-4-one | −7.3 | −43.8 |
| Nobiletin | c1c(OC)c(OC)ccc1C2=CC(=O)c3c(OC)c(OC)c(OC)c(OC)c3O2 | Flavone | 2-(3,4-Dimethoxyphenyl)-5,6,7,8-tetramethoxy-4H-1-benzopyran-4-one | −7.3 | −43.8 |
| Nodifloretin | COC1=C(C=CC(=C1)C2=CC(=O)C3=C(O2)C=C(C(=C3O)O)O)O | Flavone | 5,6,7-trihydroxy-2-(4-hydroxy-3-methoxyphenyl)chromen-4-one | −7.4 | −44.4 |
| Norartocarpetin | C1=CC(=C(C=C1O)O)C2=CC(=O)C3=C(C=C(C=C3O2)O)O | Flavone | 2-(2,4-Dihydroxyphenyl)-5,7-dihydroxy-4H-1-benzopyran-4-one | −7.8 | −46.8 |
| Norwogonin | C1=CC=C(C=C1)C2=CC(=O)C3=C(O2)C(=C(C=C3O)O)O | Flavone | 5,7,8-trihydroxy-2-phenylchromen-4-one | −7.8 | −46.8 |
| Onopordin | COC1=C(C=C(C2=C1OC(=CC2=O)C3=CC(=C(C=C3)O)O)O)O | Flavone | 2-(3,4-dihydroxyphenyl)-5,7-dihydroxy-8-methoxychromen-4-one | −7.7 | −46.2 |
| Pectolinarigenin | COC1=CC=C(C=C1)C2=CC(=O)C3=C(C(=C(C=C3O2)O)OC)O | Flavone | 5,7-Dihydroxy-6-methoxy-2-(4-methoxyphenyl)-4H-1-benzopyran-4-one | −7.4 | −44.4 |
| Pedalitin | COC1=C(C(=C2C(=C1)OC(=CC2=O)C3=CC(=C(C=C3)O)O)O)O | Flavone | 2-(3,4-dihydroxyphenyl)-5,6-dihydroxy-7-methoxychromen-4-one | −7.6 | −45.6 |
| Pilloin | COC1=C(C=C(C=C1)C2=CC(=O)C3=C(C=C(C=C3O2)OC)O)O | Flavone | 5-hydroxy-2-(3-hydroxy-4-methoxyphenyl)-7-methoxychromen-4-one | −7.8 | −46.8 |
| Primetin | C1=CC=C(C=C1)C2=CC(=O)C3=C(C=CC(=C3O2)O)O | Flavone | 5,8-dihydroxy-2-phenylchromen-4-one | −7.6 | −45.6 |
| Primuletin | C1=CC=C(C=C1)C2=CC(=O)C3=C(C=CC=C3O2)O | Flavone | 5-hydroxy-2-phenylchromen-4-one | −7.6 | −45.6 |

-continued

| Compound (ligand) | Smiles | Compound Class | IUPAC | Docking Score (kcal/mol) | Potential Total (6X Binding, kcal/mol) |
|---|---|---|---|---|---|
| Scaposin | COC1=CC(=CC(=C1OC)O)C2=CC(=O)C3=c(C(=C(C(=C3O2)OC)O)OC)O | Flavone | 5,7-dihydroxy-2-(3-hydroxy-4,5-dimethoxyphenyl)-6,8-dimethoxychromen-4-one | −7.4 | −44.4 |
| Scutellarein | C13=C(OC(=CC1=O)C2=CC=C(O)C=C2)C=C(O)C(=C3O)O | Flavone | 5,6,7-Trihydroxy-2-(4-hydroxyphenyl)-4H-1-benzopyran-4-one | −7.4 | −44.4 |
| Serpyllin | COC1=C(C(=C(C=C1)C2=CC(=O)C3=C(O2)C(=C(C=C3O)OC)OC)OC)OC | Flavone | 5-hydroxy-7,8-dimethoxy-2-(2,3,4-trimethoxyphenyl)chromen-4-one | −6.7 | −40.2 |
| Sinensetin | COC1=C(C=C(C=C1)C2=CC(=O)C3=C(C(=C(C=C3O2)OC)OC)OC)OC | Flavone | 2-(3,4-Dimethoxyphenyl)-5,6,7-trimethoxy-4H-1-benzopyran-4-one | −7.7 | −46.2 |
| Sorbifolin | COC1=C(C(=C2C(=C1)OC(=CC2=O)C3=CC=C(C=C3)O)O)O | Flavone | 5,6-dihydroxy-2-(4-hydroxyphenyl)-7-methoxychromen-4-one | −7.3 | −43.8 |
| Sudachitin | COC1=C(C=CC(=C1)C2=CC(=O)C3=C(C(=C(C(=C3O2)OC)O)OC)O)O | Flavone | 5,7-dihydroxy-2-(4-hydroxy-3-methoxyphenyl)-6,8-dimethoxychromen-4-one | −7.4 | −44.4 |
| Tangeretin | O=C2C1=C(OC)C(OC)=C(OC)C(OC)=C1OC(C3=CC=C(OC)C=C3)=C2 | Flavone | 5,6,7,8-Tetramethoxy-2-(4-methoxyphenyl)-4H-1-benzopyran-4-one | −7.7 | −46.2 |
| Techtochrysin | COC1=CC(=C2C(=C1)OC(=CC2=O)C3=CC=CC=C3)O | Flavone | 5-Hydroxy-7-methoxy-2-phenyl-4H-1-benzopyran-4-one | −7.6 | −45.6 |
| Tithonine | COC1=CC2=C(C=C1)C(=O)C=C(O2)C3=CC(=C(C=C3)OC)O | Flavone | 2-(3-hydroxy-4-methoxyphenyl)-7-methoxychromen-4-one | −7.8 | −46.8 |
| Tricetin | C1=C(C=C(C(=C1O)O)O)C2=CC(=O)C3=C(C=C(C=C3O2)O)O | Flavone | 5,7-Dihydroxy-2-(3,4,5-trihydroxyphenyl)-4H-1-benzopyran-4-one | −7.6 | −45.6 |
| Velutin | COC1=CC(=C2C(=C1)OC(=CC2=O)C3=CC(=C(C=C3)O)OC)O | Flavone | 5-hydroxy-2-(4-hydroxy-3-methoxyphenyl)-7-methoxychromen-4-one | −7.7 | −46.2 |
| Wightin | COC1=C(C2=C(C(=C1)O)C(=O)C=C(O2)C3=C(C(=CC=C3)O)OC)OC | Flavone | 5-hydroxy-2-(3-hydroxy-2-methoxyphenyl)-7,8-dimethoxychromen-4-one | −7.1 | −42.6 |
| Wogonin | COC1=C(C=C(C2=C1OC(=CC2=O)C3=CC=CC=C3)O)O | Flavone | 5,7-Dihydroxy-8-methoxy-2-phenyl-4H-1-benzopyran-4-one | −7.8 | −46.8 |
| Xanthomicrol | COC1=C(C(=C2C(=C1O)C(=O)C=C(O2)C3=CC=C(C=C3)O)OC)OC | Flavone | 5-hydroxy-2-(4-hydroxyphenyl)-6,7,8-trimethoxychromen-4-one | −7.3 | −43.8 |
| Zapotin | O=C\1c3c(OC)c(OC)ccc3O/C(=C/1)c2c(OC)cccc2OC | Flavone | 2-(2,6-Dimethoxyphenyl)-5,6-dimethoxy-4H-1-benzopyran-4-one | −6.7 | −40.2 |
| Zapotinin | COC1=C(C(=CC=C1)OC)C2=CC(=O)C3=C(O2)C=CC(=C3O)OC | Flavone | 2-(2,6-dimethoxyphenyl)-5-hydroxy-6-methoxychromen-4-one | −7.1 | −42.6 |
| Azaleatin | O=C1c3c(O/C(=C1/O)c2ccc(O)c(O)c2)cc(O)cc3OC | Flavonol | 2-(3,4-Dihydroxyphenyl)-3,7-dihydroxy-5-methoxy-4H-1-benzopyran-4-one | −7.5 | −45 |
| Fisetin | O=C1c3c(O/C(=C1/O)c2ccc(O)c(O)c2)cc(O)cc3 | Flavonol | 2-(3,4-Dihydroxyphenyl)-3,7-dihydroxy-4H-1-benzopyran-4-one | −7.5 | −45 |
| Galangin | O=C1c3c(O/C(=C1/O)c2ccccc2)cc(O)cc3O | Flavonol | 3,5,7-Trihydroxy-2-phenyl-4H-1-benzopyran-4-one | −7.3 | −43.8 |
| Gossypetin | C1=CC(=C(C=C1C2=c(C(=O)C3=C(O2)C(=C(C=C3O)O)O)O)O)O | Flavonol | 2-(3,4-Dihydroxyphenyl)-3,5,7,8-tetrahydroxy-4H-1-benzopyran-4-one | −7.5 | −45 |

-continued

| Compound (ligand) | Smiles | Compound Class | IUPAC | Docking Score (kcal/mol) | Potential Total (6X Binding, kcal/mol) |
|---|---|---|---|---|---|
| Isorhamnetin | COC1=C(C=CC(=C1)C2=C(C(=O)C3=C(C=C(C=C3O2)O)O)O)O | Flavonol | 3,5,7-Trihydroxy-2-(4-hydroxy-3-methoxyphenyl)-4H-1-benzopyran-4-one | −7.8 | −46.8 |
| Kaempferide | COC1=CC=C(C=C1)C2=C(C(=O)C3=C(C=C(C=C3O2)O)O)O | Flavonol | 3,5,7-Trihydroxy-2-(4-methoxyphenyl)-4H-1-benzopyran-4-one | −7.6 | −45.6 |
| Kaempferol | C1=CC(=CC=C1C2=C(C(=O)C3=C(C=C(C=C3O2)O)O)O)O | Flavonol | 3,5,7-trihydroxy-2-(4-hydroxyphenyl)-4H-1-benzopyran-4-one | −7.4 | −44.4 |
| Morin | O=C1c3c(O/C(=C1/O)c2ccc(O)cc2O)cc(O)cc3O | Flavonol | 2-(2,4-Dihydroxyphenyl)-3,5,7-trihydroxy-4H-1-benzopyran-4-one | −7.5 | −45 |
| Myricetin | Oc1cc(O)c2c(=O)c(O)c(oc2c1)c3cc(O)c(O)c(O)c3 | Flavonol | 3,5,7-Trihydroxy-2-(3,4,5-trihydroxyphenyl)-4H-1-benzopyran-4-one | −7.4 | −44.4 |
| Natsudaidain | COC1=C(C=C(C=C1)C2=C(C(=O)C3=C(O2)C(=C(C(=C3OC)OC)OC)OC)O)OC | Flavonol | 2-(3,4-Dimethoxyphenyl)-3-hydroxy-5,6,7,8-tetramethoxy-4H-1-benzopyran-4-one | −7.5 | −45 |
| Pachypodol | COC1=CC(=C2C(=C1)OC(=C(C2=O)OC)C3=CC(=C(C=C3)O)OC)O | Flavonol | 5-Hydroxy-2-(4-hydroxy-3-methoxyphenyl)-3,7-dimethoxy-4H-1-benzopyran-4-one | −7.3 | −43.8 |
| Rhamnazin | COC1=CC(=C2C(=C1)OC(=C(C2=O)O)C3=CC(=C(C=C3)O)OC)O | Flavonol | 3,5-Dihydroxy-2-(4-hydroxy-3-methoxyphenyl)-7-methoxy-4H-1-benzopyran-4-one | −8 | −48 |
| Rhamnetin | COC1=CC(=C2C(=C1)OC(=C(C2=O)O)C3=CC(=C(C=C3)O)O)O | Flavonol | 2-(3,4-Dihydroxyphenyl)-3,5-dihydroxy-7-methoxy-4H-1-benzopyran-4-one | −8 | −48 |
| Amurensin | CC(C)(CCC1=C(C=C(C2=C1OC(=C(C2=O)O)C3=CC=C(C=C3)O)O)O[C@H]4[C@@H]([C@H]([C@@H]([C@H](O4)CO)O)O)O)O | Flavonol glycoside | 3,5-Dihydroxy-8-(3-hydroxy-3-methylbutyl)-2-(4-hydroxyphenyl)-7-{[(2S,3R,4S,5S,6R)-3,4,5-trihydroxy-6-(hydroxymethyl)oxan-2-yl]oxy}-4H-1-benzopyran-4-one | −8 | −48 |
| Astragalin | O=C2C(\O[C@@H]1O[C@@H]([C@@H](O)[C@H](O)[C@H]1O)CO)=C(/Oc3cc(O)cc(O)c23)c4ccc(O)cc4 | Flavonol glycoside | 5,7-Dihydroxy-2-(4-hydroxyphenyl)-3-{[(2S,3R,4S,5S,6R)-3,4,5-trihydroxy-6-(hydroxymethyl)oxan-2-yl]oxy}-4H-1-benzopyran-4-one | −7.3 | −43.8 |
| Azalein | CC1C(C(C(C(O1)OC2=C(OC3=CC(=CC(=C3C2=O)OC)O)C4=CC(=C(C=C4)O)O)O)O)O | Flavonol glycoside | 2-(3,4-Dihydroxyphenyl)-5-hydroxy-7-methoxy-3-{[(2S,3R,4R,5R,6S)-3,4,5-trihydroxy-6-methyloxan-2-yl]oxy}-4H-1-benzopyran-4-one | −7.7 | −46.2 |
| Hyperoside | c1cc(c(cc1c2c(c(=O)c3c(cc(cc3O2)O)O)O[C@H]4[C@@H]([C@H]([C@H]([C@H](O4)CO)O)O)O)O)O | Flavonol glycoside | 2-(3,4-Dihydroxyphenyl)-5,7-dihydroxy-3-{[(2S,3R,4S,5R,6R)-3,4,5-trihydroxy-6-(hydroxymethyl)oxan-2-yl]oxy}-4H-1-benzopyran-4-one | −7.5 | −45 |

-continued

| Compound (ligand) | Smiles | Compound Class | IUPAC | Docking Score (kcal/mol) | Potential Total (6X Binding, kcal/mol) |
|---|---|---|---|---|---|
| Icariin | O=C3C(\O[C@@H]1O[C@H]([C@H](O)[C@@H](O)[C@H]1O)C)=C(/Oc4c(c(O[C@@H]2O[C@H](CO)[C@@H](O)[C@H](O)[C@H]2O)cc(O)c34)C\C=C(/C)C)c5ccc(OC)cc5 | Flavonol glycoside | 5-Hydroxy-2-(4-methoxyphenyl)-8-(3-methylbut-2-en-1-yl)-7-{[(2S,3R,4S,5S,6R)-3,4,5-trihydroxy-6-(hydroxymethyl)oxan-2-yl]oxy}-3-{[(2S,3R,4R,5R,6S)-3,4,5-trihydroxy-6-methyloxan-2-yl]oxy}-4H-1-benzopyran-4-one | −8.4 | −50.4 |
| Isoquercetin | C1=CC(=C(C=C1C2=C(C(=O)C3=C(C=C(C=C3O2)O)O)O[C@H]4[C@@H]([C@H]([C@@H]([C@H](O4)CO)O)O)O)O)O | Flavonol glycoside | 2-(3,4-Dihydroxyphenyl)-5,7-dihydroxy-3-{[(2S,3R,4S,5S,6R)-3,4,5-trihydroxy-6-(hydroxymethyl)oxan-2-yl]oxy}-4H-1-benzopyran-4-one | −7.2 | −43.2 |
| Kaempferitrin | CC1C(C(C(C(O1)OC2=CC(=C3C(=C2)OC(=C(C3=O)OC4C(C(C(C(O4)C)O)O)O)C5=CC=C(C=C5)O)O)O)O)O | Flavonol glycoside | 5-Hydroxy-2-(4-hydroxyphenyl)-3,7-bis{[(2S,3R,4R,5R,6S)-3,4,5-trihydroxy-6-methyloxan-2-yl]oxy}-4H-1-benzopyran-4-one | −9.4 | −56.4 |
| Miquelianin | C1=CC(=C(C=C1C2=C(C(=O)C3=C(C=C(C=C3O2)O)O)OC4C(C(C(C(O4)C(=O)O)O)O)O)O)O | Flavonol glycoside | (2S,3S,4S,5R,6S)-6-{[2-(3,4-Dihydroxyphenyl)-5,7-dihydroxy-4-oxo-4H-1-benzopyran-3-yl]oxy}-3,4,5-trihydroxyoxane-2-carboxylic acid | −7.9 | −47.4 |
| Myricitrin | CC1C(C(C(C(O1)OC2=C(OC3=CC(=CC(=C3C2=O)O)O)C4=CC(=C(C(=C4)O)O)O)O)O)O | Flavonol glycoside | 5,7-Dihydroxy-3-{[(2S,3R,4R,5R,6S)-3,4,5-trihydroxy-6-methyloxan-2-yl]oxy}-2-(3,4,5-trihydroxyphenyl)-4H-1-benzopyran-4-one | −7.5 | −45 |
| Quercitrin | C[C@H]1[C@@H]([C@H]([C@H]([C@@H](O1)OC2=C(OC3=CC(=CC(=C3C2=O)O)O)C4=CC(=C(C=C4)O)O)O)O)O | Flavonol glycoside | 2-(3,4-Dihydroxyphenyl)-5,7-dihydroxy-3-{[(2S,3R,4R,5R,6S)-3,4,5-trihydroxy-6-methyloxan-2-yl]oxy}-4H-1-benzopyran-4-one | −8 | −48 |
| Robinin | C[C@H]1[C@@H]([C@H]([C@H]([C@@H](O1)OC[C@@H]2[C@@H]([C@@H]([C@H]([C@@H](O2)OC3=C(OC4=CC(=CC(=C4C3=O)O)O[C@H]5[C@@H]([C@@H]([C@H]([c@@H](O5)C)O)O)O)C6=CC=C(C=C6)O)O)O)O)O)O)O | Flavonol glycoside | (12S,13R,14R,15R,16S,52S,53R,54S,55R,56R,82R,83R,84R,85R,86S)-13,14,15,35,53,54,55,83,84,85-Decahydroxy-32-(4-hydroxyphenyl)-16,86-dimethyl-34H-2,4,7-trioxa-3(7,3)-[1]benzopyrana-1,8(2),5(2,6)-tris(oxana)octaphan-34-one | −8.5 | −51 |
| Rutin | CC1C(C(C(C(O1)OCC2C(C(C(C(O2)OC3=C(OC4=CC(=CC(=C4C3=O)O)O)C5=CC(=C(C=C5)O)O)O)O)O)O)O)O | Flavonol glycoside | (42S,43R,44S,45S,46R,72R,73R,74R,75R,76S)-13,14,25,27,43,44,45,73,74,75-Decahydroxy-76-methyl-24H-3,6-dioxa-2(2,3)-[1]benzopyrana-4(2,6),7(2)-bis(oxana)-1(1)-benzenaheptaphane-24-one | −8.2 | −49.2 |
| Spiraeoside | c1cc(c(cc1c2c(c(=O)c3c(cc(cc3o2)O)O)O)O)O[C@H]4[C@@H]([C@H]([C@@H]([C@H](O4)CO)O)O)O | Flavonol glycoside | 3,5,7-Trihydroxy-2-(3-hydroxy-4-{[(2S,3R,4S,5S,6R)-3,4,5-trihydroxy-6-(hydroxymethyl)oxan-2-yl]oxy}phenyl)-4H-1-benzopyran-4-one | −7.9 | −47.4 |

-continued

| Compound (ligand) | Smiles | Compound Class | IUPAC | Docking Score (kcal/mol) | Potential Total (6X Binding, kcal/mol) |
|---|---|---|---|---|---|
| Troxerutin | C[C@H]1[C@@H]([C@H]([C@H]([C@@H](O1)OC[C@@H]2[C@H]([C@@H]([C@H]([C@@H](O2)Oc3c(=O)c4c(cc(cc4oc3c5ccc(c(c5)OCCO)OCCO)OCCO)O)O)O)O)O)O | Flavonol glycoside | 3',4',7-Tris[O-(2-hydroxyethyl)]rutin | −8.4 | −50.4 |
| Xanthorhamnin | CC1C(C(C(C(O1)OC2C(C(OC(C2O)OCC3C(C(C(C(O3)OC4=C(OC5=CC(=CC(=C5C4=O)O)OC)C6=CC(=C(C=C6)O)O)O)O)O)C)O)O)O)O | Flavonol glycoside | (42S,43R,44S,45R,46R,72R,73R,74R,75S,76S,92S,93R,94R,95R,96S)-13,14,25,43,44,45,73,75,93,94,95-Undecahydroxy-27-methoxy-76,96-dimethyl-24H-3,6,8-trioxa-2(2,3)-[1]benzopyrana-4(2,6),7(2,4),9(2)-tris(oxana)-1(1)-benzenanonaphan-24-one | −7.9 | −47.4 |
| Coutaric acid | c1cc(ccc1/C=C/C(=O)O[C@H]([C@H](C(=O)O)O)C(=O)O)O | Hydroxycinnamic acid | (2R,3R)-2-Hydroxy-3-{[(2E)-3-(4-hydroxyphenyl)prop-2-enoyl]oxy}butanedioic acid | −6.4 | −38.4 |
| Daidzein | O=C\1c3c(O/C=C/1c2ccc(O)cc2)cc(O)cc3 | Isoflavone | 7-Hydroxy-3-(4-hydroxyphenyl)-4H-1-benzopyran-4-one | −7.3 | −43.8 |
| Genistein | Oc1ccc(cc1)C\3=C\Oc2cc(O)cc(O)c2C/3=O | Isoflavone | 5,7-Dihydroxy-3-(4-hydroxyphenyl)-4H-1-benzopyran-4-one | −7.5 | −45 |
| Glycitein | COC1=C(C=C2C(=C1)C(=O)C(=CO2)C3=CC=C(C=C3)O)O | Isoflavone | 4',7-Dihydroxy-6-methoxyisoflavone | −7.5 | −45 |
| Glycitin | COC1=C(C=C2C(=C1)C(=O)C(=CO2)C3=CC=C(C=C3)O)O[C@H]4[C@@H]([C@H]([C@@H]([C@H](O4)CO)O)O)O | Isoflavone glucoside | 3-(4-Hydroxyphenyl)-6-methoxy-7-{[(2S,3R,4S,5S,6R)-3,4,5-trihydroxy-6-(hydroxymethyl)oxan-2-yl]oxy}-4H-1-benzopyran-4-one | −7.8 | −46.8 |
| Puerarin | C1=CC(=CC=C1C2=COC3=C(C2=O)C=CC(=C3C4C(C(C(C(O4)CO)O)O)O)O)O | Isoflavone glucoside | 7-Hydroxy-3-(4-hydroxyphenyl)-8-[(2S,3R,4R,5S,6R)-3,4,5-trihydroxy-6-(hydroxymethyl)oxan-2-yl]-4H-1-benzopyran-4-one | −7.4 | −44.4 |
| Justicidin A | COC1=C(C=C2C(=C1)C(=C3C(=C2OC)COC3=O)C4=CC5=C(C=C4)OCO5)OC | Lignan | 9-(2H-1,3-Benzodioxol-5-yl)-4,6,7-trimethoxynaptho[2,3-c]furan-1(3H)-one | −8 | −48 |
| Pinoresinol | COC1=C(C=CC(=C1)C2C3COC(C3CO2)C4=CC(=C(C=C4)O)OC)O | Lignan | (+) form: 4-[(3S,3aR,6S,6aR)-6-(4-hydroxy-3-methoxyphenyl)-1,3,3a,4,6,6a-hexahydrofuro[3,4-c]furan-3-yl]-2-methoxyphenol | −7.6 | −45.6 |
| Sesamin | c1cc2c(cc1[C@@H]3[C@H]4CO[C@@H]([C@H]4CO3)c5ccc6c(c5)OCO6)OCO2 | Lignan | 5,5'-[(1S,3aR,45,6aR)-Tetrahydro-1H,3H-furo[3,4-c]furan-1,4-diyl]bis(2H-1,3-benzodioxole) | −8.3 | −49.8 |
| 1,2,3,4,6-Pentagalloyl glucose | C1=C(C=C(C(=C1O)O)O)C(=O)OCC2C(C(C(C(O2)OC(=O)C3=CC(=C(C(=C3)O)O)O)OC(=O)C4=CC(=C(C(=C4)O)O)O)OC(=O)C5=CC(=C(C(=C5)O) | Other | (2S,3R,4S,5R,6R)-6-{[(3,4,5-Trihydroxybenzoyl)oxy]methyl}oxane-2,3,4,5-tetrayl tetrakis(3,4,5-trihydroxybenzoate) | −7.9 | −47.4 |

-continued

| Compound (ligand) | Smiles | Compound Class | IUPAC | Docking Score (kcal/mol) | Potential Total (6X Binding, kcal/mol) |
|---|---|---|---|---|---|
| | O)O)OC(=O)C6=CC(=C(C(=C6)O)O)O | | | | |
| Acutissimin A | OC1=C(C2=C(O)C(O)=C(O)C=C2C(O[C@@H]([C@H](OC3=O)[C@@H](O4)[C@@H](C5=C(O)C=C(O)C6=C5O[C@H](C7=CC=C(O)C(O)=C7)[C@@H](O)C6)C8=C(O)C(O)=C(O)C(C9=C3C %10=C(O)C(O)=C9O)=C8C4=O)[C@H](OC(C %11=C %10C(O)=C(O)C(O)=C %11)=O)COC %12=O)=O)C %12=CC(O)=C1O | Other | (1R,2R,20R,42S,46S)-46-[(2R,3S)-2-(3,4-dihydroxyphenyl)-3,5,7-trihydroxy-3,4-dihydro-2H-chromen-8-yl]-7,8,9,12,13,14,25,26,27,30,31,32,35,36,37-pentadecahydroxy-3,18,21,41,43-pentaoxanonacyclo[27.13.3.138,42.02,20.05,10.011,16.023,28.033,45.034,39]hexatetraconta-5,7,9,11,13,15,23,25,27,29(45),30,32,34(39),35,37-pentadecaene-4,17,22,40,44-pentone | −8.4 | −50.4 |
| Castavinol C3 | OC2C(O)C(O)C(OC2CO)OC4C3C(C)(C(C)=O)OC4(c(cc1OC)cc(O)c1O)Oc5c3c(O)cc(O)c5 | Other | 1-[9-(3,4-dihydroxy-5-methoxyphenyl)-3,5-dihydroxy-11-methyl-12-[3,4,5-trihydroxy-6-(hydroxymethyl)oxan-2-yl]oxy-8,10-dioxatricyclo[7.2.1.02,7]dodeca-2,4,6-trien-11-yl]ethanone | −6.9 | −41.4 |
| Grandinin | C1C2C(C3C4C(C5=C(C(=C(C(=C5C(=O)O4)C6=C(C(=C(C(=C6C(=O)O3)C7=C(C(=C(C(=C7C(=O)O2)O)O)O)O)O)O)O)O)O)C8(C(C(C(O8)CO)O)O)O)OC(=O)C9=CC(=C(C(=C9C2=C(C(=C(C=C2C(=O)O1)O)O)O)O)O)O | Other | (46R)-7,8,9,12,13,14,25,26,27,30,31,32,35,36,37-pentadecahydroxy-46-[(3R,4S)-2,3,4-trihydroxy-5-(hydroxymethyl)oxolan-2-yl]-3,18,21,41,43-pentaoxanonacyclo[27.13.3.138,42.02,20.05,10.011,16.023,28.033,45.034,39]hexatetraconta-5,7,9,11,13,15,23,25,27,29(45),30,32,34(39),35,37-pentadecaene-4,17,22,40,44-pentone | −7.8 | −46.8 |
| Grape reaction product | Oc1cc(cc(c1O)SCC(NC(=O)CCC(N)C(=O)O)C(=O)NCC(O)=O)\C=C\C(=O)OC(C(O)=O)C(O)C(O)=O | Other | 2-[(E)-3-[3-[2-[(4-amino-4-carboxybutanoyl)amino]-3-(carboxymethylamino)-3-oxopropyl]sulfanyl-4,5-dihydroxyphenyl]prop-2-enoyl]oxy-3-hydroxybutanedioic acid | −6.8 | −40.8 |
| Higenamine | Oc1ccc(cc1)CC3c2c(cc(O)c(O)c2)CCN3 | Other | 1-[(4-Hydroxyphenyl)methyl]-1,2,3,4-tetrahydroisoquinoline-6,7-diol | −7.3 | −43.8 |
| Oleuropein | CC=C1C(C(=COC1OC2C(C(C(C(O2)CO)O)O)O)C(=O)OC)CC(=O)OCCC3=CC(=C(C=C3)O)O | Other | methyl (4S,5E,6S)-4-[2-[2-(3,4-dihydroxyphenyl)ethoxy]-2-oxoethyl]-5-ethylidene-6-[(2S,3R,4S,5S,6R)-3,4,5-trihydroxy-6-(hydroxymethyl)oxan-2-yl]oxy-4H-pyran-3-carboxylate | −7.6 | −45.6 |

-continued

| Compound (ligand) | Smiles | Compound Class | IUPAC | Docking Score (kcal/mol) | Potential Total (6X Binding, kcal/mol) |
|---|---|---|---|---|---|
| Oxycinchophen | O=C(O)c1c3ccccc3nc(c1O)c2ccccc2 | Other | 3-Hydroxy-2-phenyl-4-quinolinecarboxylic acid | −8.3 | −49.8 |
| Rosmarinic acid | O=C(O)C(OC(=O)\C=C\c1ccc(O)c(O)c1)Cc2cc(O)c(O)cc2 | Other | (2R)-3-(3,4-Dihydroxyphenyl)-2-{[(2E)-3-(3,4-dihydroxyphenyl)prop-2-enoyl]oxy}propanoic aci | −6.8 | −40.8 |
| Secoisolariciresinol | COC1=C(C=CC(=C1)CC(CO)C(CC2=CC(=C(C=C2)O)OC)CO)O | Other | (2R,3R)-2,3-Bis [(4-hydroxy-3-methoxyphenyl)meth-yl]butane-1,4-diol | −6.4 | −38.4 |
| Vanillin | c1(C=O)cc(OC)c(O)cc1 | Other | 4-Hydroxy-3-methoxybenzaldehyde | −5.3 | −31.8 |
| Xanthohumol | O=C(c1c(OC)cc(O)c(c1O)C/C=C(\C)C)\C=C\c2ccc(O)cc2 | Other | 2',4,4'-Trihydroxy-6'-methoxy-3'-(3-methylbut-2-en-1-yl)chalcone | −7.5 | −45 |
| Glycitein | COC1=C(C=C2C(=C1)C(=O)C(=CO2)C3=CC=C(C=C3)O)O | Phytoestrogen | 7-Hydroxy-3-(4-hydroxyphenyl)-6-methoxy-4H-1-benzopyran-4-one | −7.4 | −44.4 |
| Secoisolariciresinol diglucoside | OC1=C(OC)C=C(C[C@H]([C@H](CO[C@H]2[C@H](O)[C@@H](O)[C@H](O)[C@@H](CO)O2)CC3=CC(OC)=C(O)C=C3)CO[C@H]4[C@H](O)[C@@H](O)[C@H](O)[C@@H](CO)O4)C=C1 | Phytoestrogen | (2R,2'R,3R,3'R,4S,4'S,5S,5'S,6R,6'R)-2,2'-[{(2R,3R)-2,3-Bis[(4-hydroxy-3-methoxyphenyl)meth-yl]butane-1,4-diyl}bis(oxy)]bis[6-(hydroxymethyl)oxane-3,4,5-triol] | −7.7 | −46.2 |
| Procyanidin B1 | O[C@H]1Cc2c(O)cc(O)c([C@@H]3[C@@H](O)[C@H](Oc4cc(O)cc(O)c34)c3ccc(O)c(O)c3)c2O[C@@H]1c1ccc(O)c(O)c1 | Proanthocyanidin | (2R,2'R,3R,3'S,4R)-2,2'-Bis(3,4-dihydroxyphenyl)-3,3',4,4'-tetrahydro-2H,2'H-[4,8'-bi-1-benzopyran]-3,3',5,5',7,7'-hexol | −8.3 | −49.8 |
| Procyanidin B3 | O[C@H]1Cc2c(O)cc(O)c([C@H]3[C@H](O)[C@H](Oc4cc(O)cc(O)c34)c3ccc(O)c(O)c3)c2O[C@@H]1c1ccc(O)c(O)c1 | Proanthocyanidin | (2R,2'R,3S,3'S,4S)-2,2'-Bis(3,4-dihydroxyphenyl)-3,3',4,4'-tetrahydro-2H,2'H-[4,8'-bi-1-benzopyran]-3,3',5,5',7,7'-hexol | −8.8 | −52.8 |
| Procyanidin B4 | O[C@@H]1Cc2c(O)cc(O)c([C@H]3[C@H](O)[C@H](Oc4cc(O)cc(O)c34)c3ccc(O)c(O)c3)c2O[C@@H]1c1ccc(O)c(O)c1 | Proanthocyanidin | (2R,2'R,3S,3'R,4S)-2,2'-Bis(3,4-dihydroxyphenyl)-3,3',4,4'-tetrahydro-2H,2'H-[4,8'-bi-1-benzopyran]-3,3',5,5',7,7'-h | −9.5 | −57 |
| Procyanidin C1 | c1cc(c(cc1[C@@H]2[C@@H](Cc3c(cc(c(c3O2)[C@H]4c5c(cc(c(c5O[C@@H]([C@@H]4O)c6ccc(c(c6)O)O)[C@H]7c8c(cc(cc8O[C@@H]([C@@H]7O)c9ccc(c(c9)O)O)O)O)O)O)O)O)O)O)O | Proanthocyanidin | (12R,13R,14R,22R,23R,24S,32R,33R)-12,22,32-Tris(3,4-dihydroxyphenyl)-12H,22H,32H-[14,28:24,38-ter-1-benzopyran]-13,15,17,23,25,27,33,35,37-nonol | −8.2 | −49.2 |
| (Z)-Resveratrol | C1=CC(=CC=C1C=CC2=CC(=CC(=C2)O)O)O | Stilbenoid | 5-[(Z)-2-(4-hydroxy-phenyl)ethenyl]benzene-1,3-diol | −6.5 | −39 |
| Astringin | O(c2cc(O)cc(\C=C\c1ccc(O)c(O)c1)c2)[C@@H]3O[C@@H][C@@H](O)[C@H](O)[C@H]3O)CO | Stilbenoid | (2S,3R,4S,5S,6R)-2-{3-[(E)-2-(3,4-Dihydroxyphenyl)ethen-1-yl]-5-hydroxyphenoxy}-6-(hydroxymethyl)oxane-3,4,5-triol | −7.9 | −47.4 |

-continued

| Compound (ligand) | Smiles | Compound Class | IUPAC | Docking Score (kcal/mol) | Potential Total (6X Binding, kcal/mol) |
|---|---|---|---|---|---|
| delta-Viniferin | C1═CC(═CC═C1[C@H]2[C@@H](C3═C(O2)C═CC(═C3)/C═C/C4═CC(═CC(═C4)O)O)C5═CC(═CC(═C5)O)O)O | Stilbenoid | 5-[(2R,3R)-5-[(1E)-2-(3,5-Dihydroxyphenyl)ethen-1-yl]-2-(4-hydroxyphenyl)-2,3-dihydro-1-benzofuran-3-yl]benzene-1,3-diol | −8.7 | −52.2 |
| epsilon-Viniferin | C1═CC(═CC═C1C═CC2═CC(═CC3═C2C(C(O3)C4═CC═C(C═C4)O)C5═CC(═CC(═C5)O)O)O)O)O | Stilbenoid | 5-{(2R,3R)-6-Hydroxy-2-(4-hydroxyphenyl)-4-[(E)-2-(4-hydroxyphenyl)ethen-1-yl]-2,3-dihydro-1-benzofuran-3-yl}benzene-1,3-diol | −8 | −48 |
| Hopeaphenol | OC(C═C1)═CC═C1[C@@H]2OC3═CC(O)═CC4═C3[C@@]2([H])C(C═C(O)C═C5O)═C5[C@@H](C6═CC═C(O)C═C6)[C@]4([H])[C@@]7([H])[C@H](C8═CC═C(O)C═C8)C9═C(C═C(O)C═C9O)[C@] %10([H])C %11═C7C═C(O)C═C %11O[C@H] %10C %12═CC═C(O)C═C %12 | Stilbenoid | 8,16-bis(4-hydroxyphenyl)-9-[4,6,12-trihydroxy-8,16-bis(4-hydroxyphenyl)-15-oxatetracyclo[8.6.1.02,7.014,17]heptadeca-2(7),3,5,10(17),11,13-hexaen-9-yl]-15-oxatetracyclo[8.6.1.02,7.014,17]heptadeca-2(7),3,5,10(17),11,13-hexaene-4,6,12-trio | −6.2 | −37.2 |
| Pallidol | C1═CC(═CC═C1C2C3C(C(C4═C3C═C(C═C4O)O)C5═CC═C(C═C5)O)C6═C2C(═CC(═C6)O)O)O | Stilbenoid | (4bR,5R,9bR,10R)-5,10-Bis(4-hydroxyphenyl)-4b,5,9b,10-tetrahydroindeno[2,1-a]indene-1,3,6,8-tetrol | −8.4 | −50.4 |
| Piceatannol | C1═CC(═C(C═C1C═CC2═CC(═CC(═C2)O)O)O)O | Stilbenoid | 4-[(E)-2-(3,5-Dihydroxyphenyl)ethen-1-yl]benzene-1,2-diol | −7.6 | −45.6 |
| Pterostilbene | O(c1cc(cc(OC)c1)\C═C\c2ccc(O)cc2)C | Stilbenoid | 4-[(E)-2-(3,5-Dimethoxyphenyl)ethen-1-yl]phenol | −7 | −42 |
| Piceid | OC1═CC(/C═C/C3═CC═C(O)C═C3)═CC(O[C@H]2[C@H](O)[C@@H](O)[C@H](O)[C@@H](CO)O2)═C1 | Stilbenoid glucoside | (2S,3R,45,5S,6R)-2-{3-Hydroxy-5-[(E)-2-(4-hydroxyphenyl)ethen-1-yl]phenoxy}-6-(hydroxymethyl)oxane-3,4,5-triol | −7.7 | −46.2 |
| (Z)-Resveratrol 4'-glucoside | C1═CC(═CC═C1C═CC2═CC(═CC(═C2)O)O)OC3C(C(C(C(O3)CO)O)O)O | Stilbenoid Metabolite | 2-[4-[(Z)-2-(3,5-dihydroxy-phenyl)ethenyl]phenoxy]-6-(hydroxymethyl)oxane-3,4,5-triol | −7.6 | −45.6 |
| cis-Resveratrol 3-sulfate | C1═CC(═CC═C1C═CC2═CC(═CC(═C2)OS(═O)(═O)O)O)O | Stilbenoid Metabolite | [3-hydroxy-5-[(Z)-2-(4-hydroxy-phenyl)ethenyl]phenyl] hydrogen sulfate | −6.6 | −39.6 |
| cis-Resveratrol 4'-sulfate | C1═CC(═CC═C1/C═C\C2═CC(═CC(═C2)O)O)OS(═O)(═O)O | Stilbenoid Metabolite | [4-[(Z)-2-(3,5-dihydroxy-phenyl)ethenyl]phenyl] hydrogen sulfate | −6.9 | −41.4 |
| Resveratrol-3-O-sulfate | C1═CC(═CC═C1C═CC2═CC(═CC(═C2)OS(═O)(═O)O)O)O | Stilbenoid Metabolite | [3-hydroxy-5-[(E)-2-(4-hydroxy-phenyl)ethenyl]phenyl] hydrogen sulfate | 7.6 | 45.6 |
| trans-Resveratrol 3,4'-disulfate | C1═CC(═CC═C1C═CC2═CC(═CC(═C2)OS(═O)(═O)O)O)OS(═O)(═O)O | Stilbenoid Metabolite | [3-hydroxy-5-[(E)-2-(4-sulfooxy-phenyl)ethenyl]phenyl] hydrogen sulfate | −8.2 | −49.2 |
| trans-Resveratrol 3,5-disulfate | C1═CC(═CC═C1C═CC2═CC(═CC(═C2)OS(═O)(═O)O)OS(═O)(═O)O)O)O | Stilbenoid Metabolite | [3-[(E)-2-(4-hydroxyphenyl)ethenyl]-5-sulfooxyphenyl] hydrogen sulfate | −7.7 | −46.2 |
| trans-Resveratrol 3-O-glucuronid | C1═CC(═CC═C1/C═C/C2═CC(═CC(═C2)O[C@H]3[C@@H]([C@H]([C@@H]([C@H](O3)C(═O)O)O)O)O)O)O | Stilbenoid Metabolite | (2S,3S,4S,5R,6S)-3,4,5-trihydroxy-6-[3-hydroxy-5-[(E)-2-(4-hydroxyphenyl)eth-enyl]phenoxy]oxane-2-carboxylic acid | −8.2 | −49.2 |

-continued

| Compound (ligand) | Smiles | Compound Class | IUPAC | Docking Score (kcal/mol) | Potential Total (6X Binding, kcal/mol) |
|---|---|---|---|---|---|
| trans-Resveratrol 4'-O-glucuronide | C1=CC(=CC=C1C=CC2=CC(=CC(=C2)O)O)OC3C(C(C(C(O3)C(=O)O)O)O)O | Stilbenoid Metabolite | (2S,3S,4S,5R,6S)-6-[4-[(E)-2-(3,5-dihydroxyphenyl)ethenyl]phenoxy]-3,4,5-trihydroxyoxane-2-carboxylic acid | −8.1 | −48.6 |
| Oleanolic acid | O=C(O)[C@@]54[C@H](/C3=C/C[C@H]1[C@](CC[C@@H]2[C@]1(C)CC[C@H](O)C2(C)C)(C)[C@]3(C)CC4)CC(C)(C)CC5 | Triterpenoid | (4aS,6aS,6bR,8aR,10S,12aR,12bR,14bS)-10-Hydroxy-2,2,6a,6b,9,9,12a-heptamethyl-1,3,4,5,6,6a,6b,7,8,8a,9,10,11,12,12a,12b,13,14b-octadecahydropicene-4a(2H)-carboxylic acid | −8.3 | −49.8 |
| Ursolic acid | O=C(O)[C@@]54[C@H](/C3=C/C[C@H]1[@](CC[C@@H]2[C@]1(C)CC[C@H](O)C2(C)C)(C)[C@]3(C)CC4)[C@@H](C)[C@H](C)CC5 | Triterpenoid | (1S,2R,4aS,6aS,6bR,8aR,10S,12aR,12bR,14bS)-10-Hydroxy-1,2,6a,6b,9,9,12a-heptamethyl-1,3,4,5,6,6a,6b,7,8,8a,9,10,11,12,12a,12b,13,14b-octadecahydropicene-4a(2H)-carboxylic acid | −8.6 | −51.6 |

However, in some embodiments, resveratrol, and epigallocatechin gallate (EGCG) are less preferred and as such excluded from certain aspects of the inventive subject matter.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. The recitation of ranges of values herein is merely intended to serve as a shorthand method of referring individually to each separate value falling within the range. Unless otherwise indicated herein, each individual value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. As also used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification or claims refer to at least one of something selected from the group consisting of A, B, C . . . and N, the text should be interpreted as requiring only one element from the group, not A plus N, or B plus N, etc.

What is claimed is:

1. A pharmaceutical composition, comprising:

an insulin complex comprising a plurality of insulin monomers, each insulin monomer comprising an A-chain and a B-chain coupled together via disulfide bonds;

a polyphenol non-covalently bound to an apical area of an interface formed by respective B-chains of a first and a second insulin monomer in the complex; and wherein at least part of the apical area is solvent exposed.

2. The composition of claim 1, wherein the insulin complex comprises six or twelve insulin monomers, and/or wherein the insulin complex has a $T_3R_3$ or $R_6$ conformation.

3. The composition of claim 1, wherein the insulin complex further comprises a divalent metal cation, and/or wherein the insulin complex further comprises a phenolic ligand in which two hydrogen bonds engage the phenolic hydroxyl group from the $A_6$ carbonyl oxygen and $A_{11}$ amide hydrogen.

4. The composition of claim 1, wherein at least one of the insulin monomers has one or more amino acid substitutions relative to a corresponding wildtype that increases serum half-life of the insulin complex, or wherein at least one of the insulin monomers has a chemical modification that increases serum half-life of the insulin complex.

5. The composition of claim 1, wherein the polyphenol binds to at least one amino acid side chain of an amino acid in a B-chain of the first insulin monomer and to at least one amino acid side chain of another amino acid in a B-chain of the second insulin monomer to thereby increase a binding interaction between the first and second insulin monomers.

6. The composition of claim 1, wherein the polyphenol binds to at least two distinct amino acid side chains of respective amino acids in a B-chain of the first insulin monomer and to at least one amino acid side chain in a B-chain of another amino acid in the second insulin monomer to thereby increase a binding interaction between the first and second insulin monomers.

7. The composition of claim 1, wherein the polyphenol binds to $B_5^{His}$ and $B_{26}^{Tyr}$ of the first insulin monomer and $B_{16}^{Tyr}$ of the second insulin monomer.

8. The composition of claim 1, wherein the polyphenol is a flavonoid, a flavonol, a (flavan-3-ol), a flavan-4-ol, a flavanone, a flavone, a flavanol, a stilbenoid polyphenol, or a curcuminoid polyphenol.

9. A method of producing a pharmaceutical composition comprising insulin, comprising:

providing an insulin complex comprising a plurality of insulin monomers, each insulin monomer comprising an A-chain and a B-chain coupled together via disulfide bonds;

combining the insulin complex with a polyphenol to produce a stabilized insulin complex, wherein the polyphenol in the stabilized insulin complex is non-covalently bound to an apical area of an interface formed by respective B-chains of a first and a second insulin monomer in the insulin complex; and wherein at least part of the apical area is solvent exposed.

10. The method of claim 9, wherein the insulin complex comprises six or twelve insulin monomers, and/or wherein the insulin complex has a $T_3R_3$ or $R_6$ conformation.

11. The method of claim 9, wherein at least one of the insulin monomers has one or more amino acid substitutions relative to a corresponding wildtype that increases serum half-life of the insulin complex, or wherein at least one of the insulin monomers has a chemical modification that increases serum half-life of the insulin complex.

12. The method of claim 9, wherein the polyphenol binds to at least one amino acid side chain of an amino acid in a B-chain of the first insulin monomer and to at least one amino acid side chain of another amino acid in a B-chain of the second insulin monomer to thereby increase a binding interaction between the first and second insulin monomers.

13. The method of claim 9, wherein the polyphenol binds to at least two distinct amino acid side chains of respective amino acids in a B-chain of the first insulin monomer and to at least one amino acid side chain of another amino acid in a B-chain of the second insulin monomer to thereby increase a binding interaction between the first and second insulin monomers.

14. The method of claim 9, wherein the polyphenol binds to $B_5^{His}$ and $B_{26}^{Tyr}$ of the first insulin monomer and $B_{16}^{Tyr}$ of the second insulin monomer.

15. The method of claim 9, wherein the polyphenol a flavonoid, a flavonol, a (flavan-3-ol), a flavan-4-ol, a flavanone, a flavone, a flavanol, a stilbenoid polyphenol, or a curcuminoid polyphenol.

16. A method of increasing storage stability of an insulin complex, comprising:

providing an insulin complex comprising a plurality of insulin monomers, each insulin monomer comprising an A-chain and a B-chain coupled together via disulfide bonds;

combining the insulin complex with a polyphenol to produce a stabilized insulin complex, wherein the polyphenol in the stabilized insulin complex is non-covalently bound to an apical area of an interface formed by respective B-chains of a first and a second insulin monomer in the insulin complex, and wherein the stabilized insulin complex has a storage stability that is greater than that of the insulin complex without the polyphenol; and wherein at least part of the apical area is solvent exposed.

17. The method of claim 16, wherein the stabilized insulin complex has at least 10% increased storage stability as compared to a corresponding insulin complex without the polyphenol.

18. The method of claim 16, wherein the insulin complex further comprises a divalent metal cation and/or a phenolic ligand in which two hydrogen bonds engage the phenolic hydroxyl group from the $A_6$ carbonyl oxygen and $A_{11}$ amide hydrogen.

19. The method of claim 16, wherein at least one of the insulin monomers has one or more amino acid substitutions relative to a corresponding wildtype that increases serum half-life of the insulin complex or wherein at least one of the insulin monomers has a chemical modification that increases serum half-life of the insulin complex.

20. The method of claim 16, wherein the polyphenol binds to $B_5^{His}$ and $B_{26}^{Tyr}$ of the first insulin monomer and $B_{16}^{Tyr}$ of the second insulin monomer, and wherein the polyphenol is a flavonoid, a flavonol, a (flavan-3-ol), a flavan-4-ol, a flavanone, a flavone, a flavanol, a stilbenoid polyphenol, or a curcuminoid polyphenol.

* * * * *